(12) United States Patent
Studzinski et al.

(10) Patent No.: US 9,233,088 B2
(45) Date of Patent: Jan. 12, 2016

(54) USE OF GLUTAMATE, GLUTAMATE DERIVATIVES OR METABOLITES, GLUTAMATE ANALOGUES OR MIXTURES THEREOF FOR THE MANUFACTURE OF A COMPOSITION FOR THE TREATMENT OF OSTEOPOROSIS

(71) Applicant: Protista Biotechnology AB, Bjuv (SE)

(72) Inventors: Tadeusz Studzinski, Lublin (PL); Jose Luis Valverde Piedra, Lublin (PL); Stefan Pierzynowski, Lund (SE)

(73) Assignee: PROTISTA BIOTECHNOLOGY AB, Bjuv (SE)

( * ) Notice: Subject to any disclaimer, the term of this patent is extended or adjusted under 35 U.S.C. 154(b) by 0 days.

(21) Appl. No.: 14/101,234

(22) Filed: Dec. 9, 2013

(65) Prior Publication Data

US 2014/0194521 A1 Jul. 10, 2014

Related U.S. Application Data

(63) Continuation of application No. 10/496,350, filed as application No. PCT/SE02/02123 on Nov. 22, 2002, now Pat. No. 6,903,981.

(30) Foreign Application Priority Data

Nov. 23, 2001 (SE) .................................. 0103932-0
Dec. 21, 2001 (SE) .................................. 0104385-0
Jun. 6, 2002 (SE) .................................. 0201713-5

(51) Int. Cl.
*A61K 31/194* (2006.01)
*A23L 1/305* (2006.01)
*A61K 31/198* (2006.01)

(52) U.S. Cl.
CPC .............. *A61K 31/194* (2013.01); *A23L 1/3051* (2013.01); *A61K 31/198* (2013.01); *A23V 2002/00* (2013.01)

(58) Field of Classification Search
CPC .................................................. A61K 31/194
See application file for complete search history.

(56) References Cited

U.S. PATENT DOCUMENTS

| | | | |
|---|---|---|---|
| 4,668,295 A | 5/1987 | Bajpai | |
| 5,296,246 A | 3/1994 | Inoue et al. | |
| 5,310,768 A | 5/1994 | Vinnars | |
| 5,646,187 A | 7/1997 | Vinnars et al. | |
| 5,817,329 A | 10/1998 | Gardiner | |
| 5,849,695 A | 12/1998 | Cohen et al. | |
| 6,451,341 B1 | 9/2002 | Slaga et al. | |

FOREIGN PATENT DOCUMENTS

| | | |
|---|---|---|
| CN | 1153634 A | 7/1997 |
| EP | 0329879 A1 | 8/1989 |
| EP | 0595345 A1 | 5/1994 |
| EP | 0605757 A1 | 7/1994 |
| JP | 4-164028 A | 6/1992 |
| JP | 6-70719 A | 3/1994 |
| JP | 2001-204441 A | 7/2001 |
| WO | 95/12991 A1 | 5/1995 |
| WO | 01/58283 A1 | 8/2001 |

OTHER PUBLICATIONS

"Australian Food and Grocery Council-Food Myths", <http://www.fagc.org.au/index.cfm?id=129>, 2003, pp. 1-4.
"Daily Glutamate Balance in Humans (Adult 60 kg)", <http:/www.ajinonnoto.com.sg/glumain.html>, copyright 2000, 1 page.
"Hidden Sources of MGS in Foods, from the Book Exictotoxins—the Taste That Kills", by Dr. Russell Blaylock, <http://www.resew.com/general35/hidd.htm>, 2005, pp. 1-5.
"IFIC Review on Mondosodium Glutamate: Examining the Myths", The Nutrition Library Review on Monosodium Glutamate: The Myths, <http://www.geocities.com/HotSprings/2455/ir-msg.html?200523>, 1994, pp. 1-14.
"NOF Ostoeporsis Prevention—Four Steps to Prevention", <http://www.hnot.org/prevention>, 2005, pp. 1-2.
"On-line Medical Dictionary", <http://cancerweb.ncl.ac.uk/cgi-bin/omd?derivative>, Nov. 18, 1997, 1 page.
"Osteoporsis Information Center, How Can You Prevent Osteoporsis", <http://www.infoaging.org/d-osteo-6-prevent.html>, Mar. 12, 2003, 1 page.
"Unique Paired Biopsy Study Shows Normal Bone Formation After Five Years of Risedronate Treatment", Bones/Orthopaedics News, Article dated Jun. 10, 2004, 5 pages.
"What Foods Should I Avoid?", http://www.msgtruth.org/avoid.htm, 2005, pp. 1-3.
Office Action received for European Patent Application No. 02791128.8, mailed on Feb. 20, 2012, 3 pages.
Final Office Action received for U.S. Appl. No. 10/496,350, mailed on Apr. 14, 2011, 8 pages.
Final Office Action received for U.S. Appl. No. 10/496,350, mailed on Aug. 1, 2011, 10 pages.
Non Final Office Action received for U.S. Appl. No. 10/496,350, mailed on Oct. 5, 2010, 8 pages.
Notice of Allowance received for U.S. Appl. No. 10/496,350, mailed on Aug. 13, 2013, 8 pages.

(Continued)

*Primary Examiner* — Thomas S Heard
(74) *Attorney, Agent, or Firm* — Morrison & Foerster LLP

(57) ABSTRACT

A method for obtaining improved bone quality in a vertebrate, including mammal and bird, the method comprising administering to a vertebrate, including mammal and bird, in a sufficient amount and/or at a sufficient rate to enable a desired effect, glutamate, glutamate derivatives or metabolites, glutamate analogues or mixtures thereof. Also contemplated is a method for modulating bone quality in a vertebrate, including mammal and bird, comprising administering to the vertebrate, including mammal and bird, in the need thereof, glutamate, glutamate derivatives or metabolites, glutamate analogues or mixtures thereof, for modulating the bone quality as well as a compositions for use in treatment.

23 Claims, 22 Drawing Sheets

(56) References Cited

OTHER PUBLICATIONS

Affinito et al., "A New Fluoride Preparation for the Prevention of Postmenopausal Osteoporosis: Calcium Monofluorophosphate", Gynecological Endocrinology, vol. 7, 1993, pp. 201-205.
Becker, C., "Pathophysiology and Clinical Manifestations of Osteoporosis", Pub Med, Aug. 1, 2006, 1 page.
Faulkner et al., "Osteoporosis; a Pediatric Concern?", Pub Med, 2007, 1 page.
Fuchs et al., "Individual and Combined Effects of Exercise and Alendronate on Bone Mass and Strength in Ovariectomized Rats", Aug. 15, 2007, 1 page.
Haoyu et al., "Effects of Mono-Sodium Glutamate Administered Neonataly on Growth and Development of Bone in Rat", Chinese Journal of Osteoporosis, vol. 6, No. 4, Nov. 2000, pp. 10-12.
Isales et al., "Future Developments in Therapy", Pub Med, Jun. 21, 2007, 1 page.
Roudier et al., "Action de l'imidazole sur l'osteoidose experimentale chez le rat, Rhumatologie (Paris)", vol. 11, No. 56, 1981, pp. 413-417.
Office Action received for Brazilian Patent Application No. PI2014364-0, mailed on Mar. 19, 2014, 2 pages.

USE OF GLUTAMATE, GLUTAMATE DERIVATIVES OR METABOLITES, GLUTAMATE ANALOGUES OR MIXTURES THEREOF FOR THE MANUFACTURE OF A COMPOSITION FOR THE TREATMENT OF OSTEOPOROSIS

CROSS REFERENCE TO RELATED APPLICATIONS

This application is a continuation of U.S. patent application Ser. No. 10/496,350, filed on May 21, 2004 (now issued as U.S. Pat. No. 8,603,981), which is a U.S. National Phase patent application of PCT/SE2002/002123, filed on Nov. 22, 2002, which claims priority to Swedish Patent Application Nos. 0201713-5, filed on Jun. 6, 2002, 0104385-0 filed on Dec. 21, 2001 and 0103932-0 filed on Nov. 23, 2001, each of which is hereby incorporated by reference in the present disclosure in its entirety.

TECHNICAL FIELD

This invention relates to a method for obtaining improved bone quality in a vertebrate, including mammal and bird. Also contemplated is a method for modulating bone quality in a vertebrate, including mammal and bird, and the manufacture of a composition for the improvement of bone quality in said vertebrate.

BACKGROUND OF THE INVENTION

The Skeleton

The skeleton is a complex organ system that is in a constant state of flux. It serves mechanical, metabolic, and protective functions. There are two types of bone; cortical and cancellous. Cortical bone is found primarily in the shafts of the long bones of the appendicular skeleton. It is also found in the outer layer of virtually all bones. Cancellous bone is found primarily in the bones of the axial skeleton and in the ends of the long bones. The cellular process of bone activity through which both cortical and cancellous bone are maintained, is referred to as bone remodelling. This remodelling takes place on bone surfaces in discrete packets known as basic multicellular units (Parfitt et al., (1987) Clin. Obstet. Gynecol. 30:786-811).

There are numerous systemic hormones, such as parathyroid hormone and vitamins such as vitamin D, calcitonin, estrogens, androgens, as well as a number of local factors, such as interleukins, transforming growth factors and prostaglandins, that play an important role in the physiology of bone remodelling.

Skeletal Disorders

Many factors contribute to the strength of the skeleton and its ability to withstand trauma without fracture. The major factor accounting for at least 70% of bone strength is bone mineral density (mass per volume). Approximately 80% of the total skeletal mass is cortical (compact) bone with a low surface: volume ratio while remaining 20% is cancellous (spongy) bone with a much higher surface: volume ratio. Alterations in the interrelationship between mass, volume, surface, and architecture are all considered in the loss of bone strength. Such a loss in bone strength will lead to an increased risk of fracture, which is one of the hallmarks of osteoporosis.

Skeletal disorders lead to a loss or weakening in bones, a condition generally termed osteoporosis.

Osteoporosis

Osteoporosis is a condition with decreased bone mass and changes in the microarchitecture of the bone, which leads to decreased strength and an increased risk for fracture.

Osteoporosis is one of the few medical conditions that affects virtually every member of the human species living beyond the age of 35. It is a major medical problem with rising medical, social, and economical consequences. Over 8 million Americans suffer from osteoporotic fractures, although the number of affected individuals is estimated to 14-25 millions using newer definitions of osteoporosis, which include those who have not yet experienced fractures but have sufficiently low bone mass to place them in potential risk groups.

The National Osteoporosis Foundation, USA, has given estimates that the cost of treating osteoporosis in 1990 was $10 billion. With the aging of the population and the increasing prevalence of osteoporosis, medical costs alone is predicted to reach $3045 billion before the year 2020 in the USA only. The World Health Organisation has proclaimed the decade 2000-2010 as the Decade of Bone and Joint Diseases.

Current therapies for treatment of osteoporosis usually acts by a mechanism of increased formation or decreased resorbtion of bone material. The effects of such treatments are summarised in table 1. Other proposed means of treating osteoporosis include calcium, exercise, and growth hormones.

TABLE 1

Common osteoporosis therapy strategies

| Strategy | Decrease resoption | Increase formation |
| --- | --- | --- |
| Effect on bone mass | Stabilize | Increase |
| Effect on bone cells | Decrease osteoclast activity | Increase osteoblast activity |
| Examples | Estrogen, calcitonin, bisphosphonates | Fluoride, Vitamin D, parathyroid hormone (PTH) |

Medical Causes of Osteoporosis

Different medical disorders may, as a secondary effect, also lead to osteoporosis. Such medical disorders are listed in Table 2.

TABLE 2

Different medical disorders causing osteoporosis

Renal

Renal failure
Idiopathic hypercalciuria
Renal tubular acidosis
Endocrine/metabolic Diabetes mellitus type I
Cushing's syndrome
Hypogonadism - primary and secondary
Hyperparathyroidism - primary and secondary
Hyperthyroidism
Homocystinuria
Acromegaly
Hypovitaminosis D
Scurvy
Hematologic/oncologic Leukemia
Lymphoma
Multiple myeloma
Waldenstrom's TABLE 2-continued Different medical disorders causing osteoporosis macroglobulinemia
Systemic mastocytosis
Hemolytic anemias
Sickle cell disease
Beta-thalassemia
PTHrP-secreting solid
tumours (esp. squamous)
renal, bladder, ovarian)
Gastrointestinal Inflammatory bowel disease
Gluten enteropathy
Postgastrectomy
Primary biliary cirrhosis
Hepatic insufficiency
Hemochromatosis
Wilson's disease
Malnutrition
Chronic inflammatory
diseases Rheumatoid arthritis
Pharmacologic agents Aluminium-containing
antacids
Anticonvulsants
Cisplatin
Cyclosporine
Glucocorticoids
Heparin
Methotrexate
Plicamycin
Thyroid hormone excess
Diuretics except thiazides
Alcohol
Other Immobilization
Osteogenesis imperfecta
Disuse/paralysis
Ehlers-Danlos syndrome
Marfans syndrome
Post organ transplantation
Pregnancy
Gaucher's disease Postmenopausal Bone Loss The last decade, the significance and concequence of postmenopausal bone loss have been idenified and defined at an international level. Medical and governmental authorities have recognised the morbidity and mortality in untreated individuals as well as the financial consequence to the society.

Known Treatment of Osteoporosis

Few drugs are currently known to increase bone formation. The most commonly used and studied drug is flouride, being able to affect both bone formation and resorption. The drug is thus widely used in modem fluorotherapy (Farley et al., Science, 222:330-332, (1983), and Umber et al., Glin. Orthop., 267:264-267), and sodium flouride is the most evaluated form.

Several studies show an increase in trabecular bone mass after long-term administration of flouride and calcium. The combination of flouride and calcium is concidered as an established treatment.

Flouride based drugs, where monofluorophospate represents the most advanced drug for fluorotherapy, show several drawbacks and often lead to complications in treated patients, e.g. gastrointestinal and rheumatic complications.

Affinito et al. have in Gynecol. Endocrinol. (7:201-205, (1993)) published a study showing an increase of 4.25% in bone mineral density after treatment of postmenopausal women with yet another form of a flouride based drug, i.e. L-glutamine calcium monofluorophospate.

Bone Problems in Birds

In chickens, hens and other broilers, such as turkeys, the weight-carrying capacity of the legs is a problem. Specifically, in several lines of turkeys gaining a body weight of more than 25 kilos bone fracture is a problem. To prevent such problems that cause unnecessary suffering of the animal as well as high costs for the farmer, there is a needs for better understanding of bone growth, bone formation and bone mineralisation.

Prophylaxis

Recent trends in the prophylaxis of the skeletal diseases demand better understanding of physiological processes of the bone formation, development and mineralization during the postnatal life of a vertebrate, including mammal and bird.

Developmental Concerns of the Skeleton

The delivery, and the consecutive hours after, are the main source of stimuli which activate functions of the digestive system, respiratory system and motion system as a function of the gravitation and dynamic load on limb bones. Additionally, there is a differentiation during the development regarding bone mass gain, muscular mass gain and fat mass gain at various stages of life.

General nutritional status, specific nutrients (e.g., zinc, glutamine), and certain tropic growth factors (e.g., growth hormone, insulin-like growth factor I, keratinocyte growth factor, and glucagon-like peptide-2) have important interactions relevant for intestinal growth and function, which, in turn, affect the development of the limb. Adequate nutritional status is critical for endogenous growth factor synthesis in the gut and other tissues and is an important mediator of organ responsiveness to exogenous growth factor administration.

It is thus highly desirable in the light of the aforementioned problems to develop means and methods for treating or preventing any condition associated with bone loss or weakening, which can also avoid problems associated with prior art means and methods. In this respect, the present invention addresses this need and interest.

SUMMARY OF THE INVENTION

In view of the foregoing disadvantages known in the art of preventing and alleviating poor bone quality and the high medical costs for doing so, as well as for correcting bone fracture associated with e.g. osteoporosis, the present invention provides new and improved methods and compositions for improving bone quality.

An object of the present invention is to provide a method for obtaining improved bone quality in a vertebrate, including mammal and bird, the method comprising administering to said vertebrate in a sufficient amount and/or at a sufficient rate to enable a desired effect, glutamate, glutamate derivates or metabolites, glutamate analogues or mixtures thereof. The a bone quality is considered improved when compared to bone quality in a vertebrate, including mammal and bird, not obtaining said glutamate, glutamate derivates or metabolites, glutamate analogues or mixtures thereof.

Thus, the method in further embodiments include a method wherein the glutamate, glutamate derivates or metabolites, glutamate analogues or mixtures thereof are selected from the group consisting of glutamate, alpha-ketoglutaric acid (AKG), ornitine-AKG, arginine-AKG, glutamine-AKG, glutamate-AKG, leucine-AKG and other salts of AKG with amino acids and amino acids derivates; mono- and di-metal salts of AKG such as CaAKG, NaAKG; mono- and di-metal salts of glutamate such as Ca-glutamate, Na-glutamate;

glutamate dipeptides and oligopeptides e.g., L-alanyl-L-glutamate, glycyl-L-glutamate and other peptides of glutamate with amino acids; glutamate dipeptides and oligopeptides e.g., glutamate-glutamine and other peptides of glutamate with other amino acids; and glutamate polymers.

The present invention also provides a method for modulating bone quality in a vertebrate, including mammal and bird, comprising administering to said vertebrate, in the need thereof, glutamate, glutamate derivates or metabolites, glutamate analogues or mixtures thereof, for modulating the bone quality.

Still furthermore, such a method for modulating bone quality is in specific embodiments a method wherein the glutamate, glutamate derivates or metabolites, glutamate analogues or mixtures thereof are selected from the group consisting of glutamate, alpha-ketoglutaric acid (AKG), ornitine-AKG, arginine-AKG, glutamine-AKG, glutamate-AKG, leucine-AKG and other salts of AKG with amino acids and amino acids derivates; mono- and di-metal salts of AKG such as CaAKG, NaAKG; mono- and di-metal salts of glutamate such as Ca-glutamate, Na-glutamate; glutamate dipeptides and oligopeptides e.g., L-alanyl-L-glutamate, glycyl-L-glutamate and other peptides of glutamate with amino acids; glutamate dipeptides and oligopeptides e.g., glutamate-glutamine and other peptides of glutamate with other amino acids; and glutamate polymers.

The invention further provides the use of glutamate, glutamate derivates or metabolites, glutamate analogues or mixtures thereof, for the manufacture of a composition for the prevention, alleviation or treatment of osteoporosis.

Still furthermore, the invention provides a use of glutamate, glutamate derivates or metabolites, glutamate analogues or mixtures thereof, for the manufacture of a composition for the modulation of bone quality in a vertebrate, including mammal and bird in the need thereof.

SHORT DESCRIPTION OF DRAWINGS

FIG. 1 is a figure showing a bone with three points marked for use in a bending test using Instron apparatus 4302, FIG. 2 is a schematic representation of the geometrical parameters of the diaphysis of a bone showing external vertical diameter B, internal vertical diameter b, external horizontal diameter H, and internal horizontal diameter h, FIG. 3 shows the bone ultimate strength ($W_f$) of humerus and femur in 35-days-old piglets when AKG is administered and where marked with an asterisk (*) $p<0.05$, FIG. 4 shows bone maximum elastic strength ($W_y$) of humerus and femur in 35-days-old piglets when AKG is administered and where marked with an asterisk (*) $p<0.05$, FIG. 5 shows the cross-sectional area of humerus and femur in 35-days-old piglets when AKG is administered and where marked with an asterisk (*) $p<0.05$, FIG. 6 shows second moment of inertia of the cross sectional area in relation to the horizontal axix ($I_x$) of humerus and femur in 35-days-old piglets when AKG is administered and where marked with an asterisk (*) $p<0.05$, FIG. 7 shows the mean relative wall thickness (MRWT) of humerus and femur in 35-days-old piglets when AKG is administered, FIG. 8 shows second moment of inertia of the cross sectional area in relation to the horizontal axix ($I_x$) of ribs in 35-days-old piglets when AKG is administered and where marked with an asterisk (*) $p<0.05$, FIG. 9 shows the cross sectional area (A) of ribs in 35-days-old piglets when AKG is administered, FIG. 10 shows the bone ultimative strength ($W_f$) of ribs in 35 days old piglets when AKG is administered and where marked with an asterisk (*) $p<0.05$, FIG. 11 shows the yielding stress of the $5^{th}$ rib in 35-days-old piglets when AKG is administered and where marked with an asterisk (*) $p<0.05$, FIG. 12 shows the moment of ultimate strength of ribs in 35-days-old piglets when AKG is administered and where marked with an asterisk (*) $p<0.05$, FIG. 13 shows the BMD of the ulna bone for the experimental right wing of the turkeys (grey bars) in group A treated with AKG or physiologic saline (PhS) and control left wing of the turkeys (open bars), FIG. 14 shows the BMD-Wi of the ulna bone for experimental right wing of the turkeys (grey bars) in group A treated with AKG or physiologic saline (PhS) and control left wing of the turkeys (open bars), FIG. 15 shows the BMD in intact (INT), shame operated (SHO), and ovariectomized (OVX) rats fed with (closed bars) or without AKG (open bars), FIG. 16 shows the effect of oral administration of AKG on the gain of bodyweight between the AKG treated (open bars) and Ala-Gln (closed bars) treated groups during the first 47 days of postnatal life. The control group is not shown, but is always less than the Ala-Gln treated groups at the different time-points measured. On day three, the difference is about 96 g, on day 14 about 690 g, on day 21 about 419 g, and on day 35 about 313 g. The absolute value of the bodyweight is shown below the bars in g.

FIG. 17 shows the bone mineral density (BMD) of the right femur at the proximal and distal metaphysis at 21 days of postnatal life. AKG treated is shown in open bars and control in closed bars, FIG. 18 shows the bone mineral density (BMD) of the right femur at the proximal and distal metaphysis at 35 days of postnatal life. AKG treated is shown in open bars and control in closed bars, FIG. 19 shows the effect of AKG administration on the level of 17-β-estradiol in blood plasma of piglets measured after 3 days, 28 days, 35 days. The absolute values of 17-β-estradiol in pg/ml is shown below each bar. The AKG treated is shown in open bars and the control in closed bars, FIG. 20 shows the effect of AKG administration on the level of osteocalcin in blood plasma of piglets measured after 3 days, 28 days, 35 days, 56 days and 70 days. The absolute values of osteocalcin in ng/ml is shown below each bar. The AKG treated is shown in open bars and the control in closed bars, FIG. 21 shows the effect of Ala-Gln administration on the level of 17-β-estradiol in blood plasma of piglets measured after 3 days, 28 days, 35 days. The absolute values of 17-β-estradiol in pg/ml is shown below each bar. The Ala-Gln treated is shown in open bars and the control in closed bars, and FIG. 22 shows the effect of Ala-Gin administration on the level of osteocalcin in blood plasma of piglets measured after 3 days, 28 days, 35 days, 56 days and 70 days. The absolute values of osteocalcin in ng/ml is shown below each bar. The Ala-Gln treated is shown in closed bars and the control in open bars.

DETAILED DESCRIPTION OF THE INVENTION

Definitions

As used herein, the term "bone quality" is intended to mean mechanical, chemical and physiological characteristics of the bone as measured by certain parameters used according to the invention. Such parameters are known to the skilled man in the art and are further defined upon usage in the text The term "improved bone quality" is herein intended to mean changes in the mechanical, chemical and physiological characteristics of a bone, thus defining the quality of the bone, compared to a vertebrate, not obtaining treatment or administration according to the invention. The changes are regarded as an improvement if such changes are positive for said vertebrate.

The term "modulating bone quality" is herein intended to mean changing, modifying or otherwise influencing the current mechanical, chemical and physiological characteristics of a bone.

As used herein, "pharmaceutical composition" means therapeutically effective composition according to the invention.

A "therapeutically effective amount", or "effective amount", or "therapeutically effective", as used herein, refers to that amount which provides a therapeutic effect for a given condition and administration regimen. This is a predetermined quantity of active material calculated to produce a desired therapeutic effect in association with the required additive and diluent; i.e., a carrier, or administration vehicle. Further, it is intended to mean an amount sufficient to reduce and most preferably prevent, a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent; i.e., carrier, or additive.

As used herein, "treating", means treating for curing which may be a full curing or a partial curing of a condition or conditions associated with bone loss or weakening.

As used herein "alleviation", means a decreased, i.e. less, or milder condition or conditions associated with bone loss or weakening.

As used herein "preventing", means a complete or partial block of development, or outbreak, of a certain condition or conditions associated with bone loss or weakening.

The term "derviate" or "derivative" is herein intended to mean a chemical substance derived from mother substance either directly or by modification or partial substitution.

The term "analogue" or analog" is herein intended to mean compounds that are structurally similar to another, but are not necessarily isomers. Analogs have similar function(s) but differ in structure or evolutionary origin.

In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art.

Bone Development

The rapid growth and development of the gastro intestinal tract, GIT, and limb bones in new-born vertebrate, including mammals, such as humans and piglets, and birds, such as hens and turkeys, is connected with increased intestinal requirement and cellular demand for metabolic energy supplied mainly for the enterocytes and osteocytes.

To date, no comprehensive investigation has been conducted on the nutritional effects of drugs based on glutamate, glutamate derivate, metabolites, or analogues on growth, development and mineralization of the skeletal system during the postnatal period.

Glutamate derivate, metabolites, or analogues are e.g. alpha-ketoglutaric acid (AKG), and derivates, metabolites and analogues of AKG as described and exemplified in further detail below. Flouride based drugs, such as L-glutamine calcium monofluorofosfate, representing the currently used drugs for treatment of bone loss and weakening, in e.g. osteoporosis, are thus not included in the current invention. The effect, as well as side effects, of fluoride is partially different from glutamate, glutamate derivate, metabolites, or analogues.

As revealed above, the present invention relates to means and methods for treating, alleviating or preventing any condition associated with bone loss or weakening. Conditions that are associated with bone loss or weakening, such as in osteoporosis, are, but not limited to, renal, such as renal failure, idiopathic hypercalciuria, renal tubular acidosis; endocrine or metabolic, such as diabetes mellitus type I, Cushing's syndrome, hypogonadism—primary and secondary, hyperparathyroidism - primary and secondary, hyperthyroidism, homocystinuria, acromegaly, hypovitaminosis D, scurvy; hematologic/oncologic, such as leukemia, lymphoma, multiple myeloma, Waldenstrom's macroglobulinemia, systemic mastocytosis, hemolytic anemias, sickle cell disease, Beta-thalassemia, PTHrP-secreting solid tumours (e.g. squamous renal, bladder, ovarian); gastrointestinal, such as inflammatory bowel disease, gluten enteropathy, postgastrectomy, primary biliary cirrhosis, hepatic insufficiency, hemochromatosis, Wilson's disease, malnutrition; chronic inflammatory diseases, such as rheumatoid arthritis; . pharmacologic agents, such as aluminium-containing antacids, anticonvulsants, cisplatin, cyclosporine, glucocorticoids, heparin, methotrexate, plicamycin, thyroid hormone excess, diuretics except thiazides, alcohol; and others, such as immobilization, osteogenesis imperfecta, disuse/paralysis, Ehlers-Danlos syndrome, Marfans syndrome, post organ transplantation, pregnancy, and Gaucher's disease.

Bone Fractures

Bone fractures may cause so called functional osteoporosis, not only at the site of the fracture but in other bones in the body as well. Alterations in the interrelationship between mass, volume, surface, and architecture are all factors considered in the loss of bone strength. A loss in bone strength will lead to a further increased risk for a fracture, which is one of the hallmarks of osteoporosis.

Other situations causing changes, e.g. loss, in bone strength are hospitalisation as in long-stay care; involuntary immobilisation, such as a human being in a wheel chair or having a plaster; voluntary immobilisation, such as a sedentary work or a sedentary life; changes in gravity field as for e.g. astronouts.

A Method for Obtaining Improved Bone Quality

According to the invention a method is used for obtaining improved bone quality in a vertebrate, including mammal and bird, the method comprising administering to said vertebrate, in a sufficient amount and/or at a sufficient rate to enable a desired effect, glutamate, glutamate derivates or metabolites, glutamate analogues or mixtures thereof, as compared to changes in a vertebrate, including mammal and bird, not obtaining said glutamate, glutamate derivates or metabolites, glutamate analogues or mixtures thereof. The changes in bone quality in the treated vertebrate is compared to changes in bone quality of a vertebrate, including mammal and bird, not obtaining said glutamate, glutamate derivates or metabolites, glutamate analogues or mixtures thereof and regarded as an improvement if such changes are positive for the vertebrate, including mammals, such as a piglet or human, and birds, such as hens and turkeys, being in the need thereof.

In different embodiments of the invention, the method above is a method wherein the glutamate, glutamate derivates or metabolites, glutamate analogues or mixtures thereof are selected from the group consisting of glutamate, alpha-ketoglutaric acid (AKG), ornitine-AKG, arginine-AKG, glutamine-AKG, glutamate-AKG, leucine-AKG and other salts of AKG with amino acids and amino acids derivates; mono- and di-metal salts of AKG such as CaAKG, NaAKG; mono- and di-metal salts of glutamate such as Ca-glutamate, Na-glutamate; glutamate dipepetides and oligopeptides e.g., L-alanyl-L-glutamate, glycyl-L-glutamate and other peptides of glutamate with amino acids; glutamate dipeptides and oligopeptides e.g., glutamate-glutamine and other peptides of glutamate with other amino acids; and glutamate polymers.

In further embodiments of the invention, the vertebrate, used in the above method the vertebrate is a rodent, such as a mouse, rat, guinea pig, or a rabbit; a bird, such as a turkey, hen, chicken or other broilers; farm animals, such as a cow, a horse, a pig, piglet or free going farm animals; or a pet, such as a dog, or a cat.

In still an even further embodiment, the vertebrate is a human being. The human being may be a patient in the need of treatment of bone loss or weakening, e.g. due to osteoporosis, or due to a bone fracture. A bone fracture is a traumatic disruption of the continuity of a bone. In even further embodiments, the bone loss or weakening is due to overloading the bones, e.g., as in sport, due to overweight or a handicap.

A Method for Modulating Bone Quality

According to the invention, a method for modulating bone quality in a vertebrate, including mammal and bird, comprises administering to said vertebrate in the need thereof, glutamate, glutamate derivates or metabolites, glutamate analogues or mixtures thereof, for modulating the bone quality.

In further embodiments of the invention, such a method for modulating bone quality is a method wherein the glutamate, glutamate derivates or metabolites, glutamate analogues or mixtures thereof are selected from the group consisting of glutamate, alpha-ketoglutaric acid (AKG), ornitine-AKG, arginine-AKG, glutamine-AKG, glutamate-AKG, leucine-AKG and other salts of AKG with amino acids and amino acids derivates; mono- and di-metal salts of AKG such as CaAKG, NaAKG; mono- and di-metal salts of glutamate such as Ca-glutamate, Na-glutamate; glutamate dipepetides and oligopeptides e.g., L-alanyl-L-glutamate, glycyl-L-glutamate and other peptides of glutamate with amino acids; glutamate dipeptides and oligopeptides e.g., glutamate-glutamine and other peptides of glutamate with other amino acids; and glutamate polymers.

In even further embodiments of the invention, the vertebrate, including mammal and bird, used in the above method is a rodent, such as a mouse, rat, guinea pig, or a rabbit; a bird, such as a turkey, hen, chicken or other broilers; farm animals, such as a cow, a horse, a pig, piglet or free going farm animals; or a pet, such as a dog, or a cat.

In still an even further embodiment, the vertebrate is a human being. The human being may be a patient in the need of treatment of bone loss or weakening, e.g. due to osteoporosis, or due to a bone fracture. A bone fracture is a traumatic disruption of the continuity of a bone. In even further embodiments, the bone loss or weakening is due to overloading the bones e.g. as in sport, due to overweight or a handicap.

A Method Inhibition of Bone Resorption

According to the invention, a method for inhibition of bone resorption in a vertebrate, including mammal and bird, comprises administering to said vertebrate in the need thereof glutamate, glutamate derivates or metabolites, glutamate analogues or mixtures thereof, for modulating the bone quality.

In further embodiments of the invention, such a method for inhibition of bone resorption is a method wherein the glutamate, glutamate derivates or metabolites, glutamate analogues or mixtures thereof are selected from the group consisting of glutamate, alpha-ketoglutaric acid (AKG), ornitine-AKG, arginine-AKG, glutamine-AKG, glutamate-AKG, leucine-AKG and other salts of AKG with amino acids and amino acids derivates; mono- and di-metal salts of AKG such as CaAKG, NaAKG; mono- and di-metal salts of glutamate such as Ca-glutamate, Na-glutamate; glutamate dipepetides and oligopeptides e.g., L-alanyl-L-glutamate, glycyl-L-glutamate and other peptides of glutamate with amino acids; glutamate dipeptides and oligopeptides e.g., glutamate-glutamine and other peptides of glutamate with other amino acids; and glutamate polymers.

In even further embodiments of the invention, the vertebrate, including mammal and bird, used in the above method, is a rodent, such as a mouse, rat, guinea pig, or a rabbit; a bird, such as a turkey, hen, chicken or other broilers; farm animals, such as a cow, a horse, a pig, piglet or free going farm animals; or a pet, such as a dog, or a cat.

In still an even further embodiment, the vertebrate is a human being. The human being may be a patient in the need of treatment of bone loss or weakening, e.g., due to osteoporosis.

Administration of Glutamate, Glutamate Derivates or Metabolites, Glutamate Analogues or Mixtures Thereof According to the methods disclosed above, glutamate, glutamate derivates or metabolites, glutamate analogues or mixtures thereof, is administered to a vertebrate, including mammal and bird; a rodent, such as a mouse, rat, guinea pig, or a rabbit; a bird, such as a turkey, hen, chicken or other broilers; farm animals, such as a cow, a horse, a pig, piglet or free going farm animals; or a pet, such as a dog, or a cat.

Administration may be performed in different ways depending on what species of vertebrate to treat, the condition of the vertebrate in the need of said methods, and the specific indication to treat.

In one embodiment, the administration is done as a food or feed supplement, such as a dietary supplement and/or a component in form of solid food and/or beverage. Further embodiments may be in the form of suspensions or solutions, such as a beverage further described below.

Also, the dosage forms may include capsules or tablets, such as chewable or soluble, e.g. effervescent tablets, as well as powder and other dry formats known to the skilled man in the art, such as pellets, such as micropellets, and grains.

The administration may be in the form of parenteral, rectal or oral food or feed supplement, as revealed above. Parenteral vehicles include sodium chloride solution, Ringer's dextrose, dextrose and sodium chloride, lactated Ringer's or fixed oils.

The food and feed supplement may also be emulsified. The active therapeutic ingredient may then be mixed with excipients, which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH, buffering agents, which enhance the effectiveness of the active ingredient.

Different formats of the parenteral food or feed supplement may be supplied, such as solid food, liquids or lyophilized or otherwise dried formulations. It may include diluents of various buffers (e.g., Tris-HCL, acetate, phosphate), pH and ionic strength, additives such as albumin or gelatine to prevent absorption to surfaces, detergents (e.g., Tween 20, Tween80, Pluronic F68, bile acid salts). solubilizing agents (e.g., glycerol, polyethyleneglycerol), anti-oxidants (e.g., ascorbic acid, sodium metabisulfite), preservatives (e.g.,Thimerosal, benzyl alcohol, parabens), bulking substances or tonicity modifiers (e.g., lactose, mannitol), covalent attachment of polymers such as polyethylene glycol to the composition, complexation with metal ions, or incorporation of the material into or onto particulate preparations of polymeric compounds such as polylactic acid, polglycolic acid, hydrogels, etc., or onto liposomes, microemulsions, micelles, unilamellar or multilamellarvesicles, erythrocyte ghosts, or spheroplasts.

A beverage

In one embodiment, the food or feed supplement is administered in the form of a beverage, or a dry composition thereof, in any of the methods according to the invention.

The beverage comprises an effective amount of glutamate, glutamate derivates or metabolites, glutamate analogues or a water-soluble innocuous salt thereof, or mixtures thereof, together with a nutritionally acceptable water-soluble carrier, such as minerals, vitamins, carbohydrates, fat and proteins. All of these components are supplied in a dried form if the beverage is provided in a dry form. A beverage provided ready for consumption further comprises water. The final beverage solution may also have a controlled tonicity and acidity, e.g. as a buffered solution according to the general suggestions in the paragraph above.

The pH is preferably in the range of about 2-5, and in particularly about 2-4, to prevent bacterial and fungal growth. A sterilised beverage may also be used, with a pH of about 6-8.

The beverage may be supplied alone or in combination with one or more therapeutically effective composition(s).

Use of Glutamate, Glutamate Derivatives or Metabolites, Glutamate Analogues or Mixtures Thereof According to the invention, a use of glutamate, glutamate derivatives or metabolites, glutamate analogues or mixtures thereof, are disclosed for the manufacture of a composition for the prevention, alleviation or treatment of osteoporosis.

Further embodiments of the invention includes a use, wherein the composition is a pharmaceutical composition. This pharmaceutical composition may be together with a pharmaceutically acceptable carrier and/or additives, such as diluents, preservatives, solubilizers, emulsifiers, adjuvants and/or carriers useful in the methods and use disclosed in the present invention.

Further, as used herein "pharmaceutically acceptable carriers" are well known to those skilled in the art and may include, but are not limited to, 0.01- 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Even further embodiments of the invention includes a use, wherein the composition is a dietary supplement and/or a component in the form of solid food and/or beverage.

Such a manufactured composition, such as a pharmaceutical composition or a food or feed supply, comprises the use according to manufacture a composition according to the invention, and may optionally comprise a carrier and/or an amount of a second or further active ingredient affecting osteoporosis.

Improving Bone Quality

Still, another use according to the invention is the use of glutamate, glutamate derivates or metabolites, glutamate analogues or mixtures thereof, for the manufacture of a composition for the improvement of bone quality in a subject in the need thereof.

Further embodiments of the invention include a composition, wherein the composition is a pharmaceutical composition. This may be together with a pharmaceutically acceptable carrier and/or additives, such as diluents, preservatives, solubilizers, emulsifiers, adjuvants and/or carriers useful in the methods and use disclosed in the present invention.

Further, as used herein "pharmaceutically acceptable carriers" are well known to those skilled in the art and may include, but are not limited to, 0.01- 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Even further embodiments of the invention includes a use, wherein the composition is a dietary supplement and/or a component in the form of solid food and/or beverage.

Such a manufactured composition, such as a pharmaceutical composition or a food or feed supply, comprises the use according to manufacture a composition according to the invention, and may optionally comprise a carrier and/or an amount of a second or further active ingredient affecting osteoporosis.

Dose of the Administered Pharmaceutical Composition

According to the invention, the use of use of glutamate, glutamate derivatives or metabolites, glutamate analogues or mixtures thereof for the manufacture of a composition according to the invention includes to administer a therapeutical effective amount to the vertebrat, such as a bird or mammal in the need thereof. Such a therapeutically effective amount is about 0.01-0.2 g/kg bodyweight per daily dose.

Administration Targets

As can be readily appreciated by one of ordinary skill in the art, the methods and pharmaceutical compositions of the present invention are particularly suited for administration to any animal in the need thereof, particularly a bird, including but not limited to, a turkey, hen or chicken and other broilers and free going animals, or a mammal, including but not limited to, domestic animals, such as feline or canine subjects, farm animals, such as, but not limited to, bovine, equine, caprine, ovine, and porcine subjects, wild animals, whether in the wild or in a zoological garden, research animals, such as mice, rats, rabbits, goats, sheep, pigs, dogs, cats, etc., i.e. for veterinary medical use.

Also, human beings are included as administration targets in the treatment of bone loss or weakening, such as osteoporosis or bone fracture.

Use of the Invention for Prevention and Repair of Bone Fractures

According to the invention, a use of glutamate, glutamate derivates or metabolites, glutamate analogues or mixtures thereof, in included for the manufacture of a composition for the prevention or repair of bone fractures in a vertebrate, including mammal and bird, in the need thereof.

The use for the prevention or repair of bone fractures may be wherein the composition is a pharmaceutical composition with optionally a pharmaceutically acceptable carrier and/or additives.

Furthermore, the use for the prevention or repair of bone fractures may include a composition being a food or a feed supplement, or a dietary supplement and/or a component in form of solid food and/or beverage.

Even further embodiments include the use for the prevention or repair of bone fractures, wherein glutamate, glutamate derivates or metabolites, glutamate analogues or mixtures thereof, in the manufactured composition is in a therapeutically effective amount. In one embodiment, the therapeutically effective amount is 0.01-0.2 g/kg bodyweight per daily dose.

3—Third group, receiving 0.4 g/kg/b.w. α-keto-glutaric sodium salt, AKG, (2 ml solution /kg b.w.) once a day from the first day to the 35$^{th}$ day of life.

The experimental protocol is summarised in table 3.

Parameters for Measuring Bone Quality

Different parameters are used for defining and measuring the bone quality according to the invention. Used parameters are known to the skilled man in the art and are explained below:
1) Maximum elastic strength measures the load, in Newtons (N), at a fracture.
2) Ultimate strength measures the load, in Newtons (N), at a fracture of the bone.
3) Cross-sectional area is the measure of the bone area on the cross section, in $mm^2$.
4) Second moment of inertia is the measurement of the efficiency of the cross-sectional geometry to resist bending force, expressed in $mm^4$.
5) Mean relative wall thickness is the wall thickness of the bone to its lumen.
6) Bone mineral density (BMD) expresses the mineral content of the bone expressed in $g/cm^2$.

TABLE 3

Experimental protocol

| Treatment | | Control group (Saline) | L-alanyl-L-glutamine (Ala-Gln group) | α-Ketoglutarate (AKG) |
|---|---|---|---|---|
| 1-28 days | Sow milk + | 2 ml solution/ kg.bw. oral admin. | 0.4 g/kg/b.w. (2 ml solution/ kg b.w.) oral admin. | 0.4 g/kg/b.w. (2 ml solution/ kg b.w) oral admin. |
| | Weaning | | | |
| 28-35 days | Premix prestarter (PP) + water ad. lib. + | 2 ml solution/ kg.bw. oral admin. | 0.4 g/kg/b.w. Ala-gln (2 ml solution/ kg b.w.) oral admin. | 0.4 g/kg/b.w. (2 ml solution/ kg b.w.) oral admin. |
| n = | | 8 | 8 | 7 |

EXAMPLES

Example 1

The Influence of L-alanyl-L-glutamine (Ala-Gln) and α-keto-glutaric Acid (AKG) on Growth, Development and Mineralization of the Skeletal System During the Postnatal Life in the Pig Animal Maintenance Piglets obtained from the University herd, Czeslawice, Poland were kept in standard fanning conditions.

Animal Experiments

All piglets suckled sow milk before weaning. After weaning at the age of 28 days piglets were fed ad libitum with a standard mixture Premix prestarter (PP) (Food plant-Motycz, Poland) and free access to water was allowed. Piglets were allotted to three experimental trials:
1—Control group, receiving saline (2 ml/kg body weight (b.w.))
2—Second group, receiving 0.4 g/kg/b.w. of L-alanyl-L-glutamine (ala-gln), (2 ml solution/kg b.w.)

Animal weight gain was monitored every day before oral administration of saline, ala-gln or AKG. At the age of 35 days, piglets were sacrificed, eviscerated and bones were sampled.

Architectural and geometric properties of bone were estimated based on measurements of horizontal and vertical cross section as well as interior and exterior diameter of the bone.

Using Instron 4302 apparatus and applying three point bending test as presented in FIG. 1, the following properties of the bones were determined from curves showing the relation between load and deflection:
1) maximum elastic strength, $W_y$
2) ultimate strength, $W_f$
3) bone stiffness
4) maximum elastic deflection.

Results

Bone Properties

Bone ultimate strength, maximum elastic strength, maximum elastic deflection, bone stiffness and mean relative wall thickness (MRWT) were analysed.

FIG. 2 shows a schematic representation of the geometrical parameters of the diaphysis of the bone.

Mean relative wall thickness (MRWT) expresses the ratio of wall to lumen measures and serves as an indicator in the process of architectural adaptation of bone to physiological stress during the growth of the body. When the lumen increases with unchanged wall thickness the MRWT decreases but bone resistance to strain increases.

Bone Ultimate Strength

Bone ultimate strength ($W_f$) of humerus did not differ significantly between the control group and the Ala-Gln group, while this parameter was significantly higher in the AKG group when compared both to the piglets of the control and Ala-Gln groups (Table 4 and FIG. 3).

Femur ultimate strength was the lowest in the piglets of the control group.

Significantly higher values of this parameter were present in both experimental groups when compared to the control (Table 9 and FIG. 3).

TABLE 4

Bone ultimate strength ($W_f$) of humerus and femur from control and experimental piglets at the age of 35 days of postnatal life

| 35 days | Bone ultimate strength ($W_f$) [N] | |
|---|---|---|
| | humerus mean ± SEM | femur mean ± SEM |
| Control | 747.4 ± 3.89 | 930.5 ± 70.23 |
| Ala-Gln | 743.0 ± 15.71 V | 1075.0 ± 28.16 * |
| AKG | 857.6 ± 45.42 * | 1123.0 ± 75.09 * |

\* p < 0.05 AKG versus control,
∇ p < 0.05 AKG versus Ala-Gln

Bone Maximum Elastic Strength

Bone maximum elastic strength (W)) of humerus and femur of both Ala-Gln and AKG group were significantly higher in comparison to that of the control (Table 5 and FIG. 4)

TABLE 5

Bone maximum elastic strength ($W_y$) of humerus and femur from control and experimental piglets at 35 days of postnatal life

| 35 days | Bone maximum elastic strength ($W_y$) [N] | |
|---|---|---|
| | humerus mean ± SEM | femur mean ± SEM |
| Control | 604.2 ± 26.25 | 921.1 ± 62.53 |
| Ala-Gln | 638.7 ± 9.91 * | 1016.8 ± 46.68 * |
| AKG | 726.0 ± 37.73 * | 1042.9 ± 73.66 * |

\* p < 0.05 experimental versus control

Cross-Sectional Area

Cross-sectional area (A) of humerus and femur were significantly higher in the piglets of both experimental groups when compared to that of the control (Table 6 and FIG. 5).

TABLE 6

Cross-sectional area (A) of humerus and femur from control and experimental piglets at 35 days of postnatal life

| 35 days | Cross-sectional area (A) [mm$^2$] | |
|---|---|---|
| | humerus mean ± SEM | femur mean ± SEM |
| Control | 42.7 ± 3.52 | 49.9 ± 3.38 |
| Ala-Gln | 52.2 ± 2.48 * | 60.1 ± 2.59 * |
| AKG | 52.7 ± 4.1 * | 64.7 ± 3.82 * |

\* p < 0.05 experimental versus control

Second Moment of Inertia

Second moment of inertia of the cross sectional area in relation to the horizontal axis (Ix) of humerus was significantly higher in both Ala-Gln and AKG group in comparison to control group (Table 7 and FIG. 6). Second moment of inertia of the femur was significantly different in the AKG group in comparison to both control and Ala-Gln groups (Table 7 and FIG. 6).

TABLE 7

Second moment of inertia [mm$^4$] of humerus and femur from control and experimental piglets at 35 days of postnatal life

| | Second moment of inertia (Ix) [mm$^4$] | |
|---|---|---|
| 35 days | HUMERUS mean ± SEM | FEMUR mean ± SEM |
| Control | 287.5 ± 24.65 | 452.3 ± 49.28 |
| Ala-Gln | 368.4 ± 24.31 * | 492.8 ± 12.81 V |
| AKG | 459.4 ± 59.42 * | 696.5 ± 48.7 * |

\* p < 0.05 AKG versus control,
∇ p < 0.05 AKG versus Ala-Gln

Mean Relative Wall Thickness

Mean relative wall thickness (MRWT) of humerus and femur of the bones of the piglets receiving Ala-Gln and AKG showed a tendency toward higher values; however, the differences were not significant (Table 8 and FIG. 7).

TABLE 8

Mean relative wall thickness (MRWT) of humerus and femur from control and experimental piglets at 35 days of postnatal life

| | Mean Relative wall thickness (MRWT) | |
|---|---|---|
| 35 days | humerus mean ± SEM | femur mean ± SEM |
| Control | 0.52 ± 0.09 | 0.62 ± 0.06 |
| Ala-Gln | 0.64 ± 0.07 | 0.88 ± 0.12 |
| AKG | 0.57 ± 0.08 | 0.70 ± 0.07 |

Second Moment of Inertia ($I_x$) of the Cross Sectional Area in Relation to the Horizontal Axis of Ribs Second moment of inertia ($I_x$) of the cross sectional area in relation to the horizontal axis of ribs was significantly higher in the AKG group when compared both to the control and Ala-Gin group. Cross sectional area of ribs in the AKG group was also significantly different in comparison to the control group. Mean relative wall thickness (MRWT) was the lowest in the ribs of piglets receiving AKG, intermediate for the control group and the highest for Ala-Gln group (Table 9 and FIG. 8).

TABLE 9

Second moment of inertia ($I_x$), cross-sectional area (A), mean relative wall thickness (MRWT) of ribs (4-9) of piglets at the age of 35 days of postnatal life

| | Second moment of inertia [mm$^4$] (ribs 4-9) Mean ± SEM | Cross sectional area (A) [mm$^2$] (ribs 4-9) Mean ± SEM | MRWT (ribs 4-9) Mean ± SEM |
|---|---|---|---|
| Control | 10.46 ± 0.66 | 9.43 ± 0.34 | 0.65 ± 0.037 |
| Ala-Gln | 10.88 ± 0.55 | 9.62 ± 0.33 | 0.70 ± 0.038 |
| AKG | 15.42 ± 0.93 * | 10.52 ± 0.35 * | 0.60 ± 0.026 |

\* p < 0.05

Bone Ultimate Strength ($W_f$), Maximum Elastic Strength and Moment of Ultimate Strength of Ribs Bone ultimate strength ($W_f$) of ribs from the 4$^{th}$ to the 9$^{th}$ was the highest in the AKG treated piglets and significantly different from that of the control group (table 10 and FIG. 10).

Moment of ultimate strength was significantly higher in the AKG group in comparison to both control and Ala-Gln values, which is shown in FIG. 12 as well as table 10.

Maximum elastic strength ($W_y$) was significantly higher in the AKG group when compared to the control group (Table 10).

Cross sectional area (A) of ribs (from the 4$^{th}$ to the 9$^{th}$) from control and experimental piglets at the age of 35 days of postnatal life is shown in FIG. 9, where AKG treated animals showed the largest change in area with a p<0.05.

TABLE 10

Bone ultimate strength ($W_f$), moment of ultimate strength and bone maximum elastic strength ($W_y$) of 4$^{th}$ to 9$^{th}$ ribs of piglets at the age of 35 days of postnatal life

|  | Ultimate strength (Wf) [N] (ribs 4-9) Mean ± SEM | Moment of ultimate strength [N] ribs (4-9) Mean ± SEM | Bone maximum elastic strength ($W_y$)[N] (ribs 4-9) Mean ± SEM |
|---|---|---|---|
| Control | 463.1 ± 23.5 | 612.86 ± 32.37 | 423.6 ± 18.97 |
| Ala-Gln | 450.2 ± 22.1 | 625.24 ± 1.5 V | 442.9 ± 15.32 |
| AKG | 585.1 ± 18.5 * | 737.445 ± 23.85 * | 522.5 ± 17.97 * | p < 0.05

Yielding Stress

The yielding stress of the 5$^{th}$ rib was measured and the results for 35-days-old piglets of control and experimental groups are given in FIG. 11, showing a significant increase in the AKG treated group. Thus, the bones are stronger.

Example 2

The Effect of AKG on the Ulna Mineralisation, Mechanical and Geometrical Properties After Fracture and Neurectemy of the Radial and Mediouluar Nerve in the Turkey Objective The objective of this example is to study the effects of AKG on geometrical and physical poperties of bones and callus formation and the influence of the nervous system on bone growth based on analysis of turkey wing bone (ulna).

Animal Maintenance

Turkeys are kept in common cages, 10 turkeys/cage. The turkeys have free access to water and are fed ad libitum.

Experimental Design

A total of 160 turkeys at the age of 6 weeks are devided into four experimental groups, each with a different treatment according to table 11.

TABLE 11

Experimental design

| Group A | Right | Neurectomized - right N. radial, medioulnar Fracture of the ulnae | PhS[a] AKG |
|---|---|---|---|
|  | Left | Control intact | PhS AKG |
| Group B | Right[b] | Fracture of the ulnae | PhS AKG |
|  | Left[b] | Control intact | PhS AKG |

TABLE 11-continued

Experimental design

| Group C | Right | Neurectomized - right N. radial. medioulnar | PhS AKG |
|---|---|---|---|
|  | Left | Control intact | PhS AKG |
| Group D | Right | Shame operated | PhS AKG |
|  | Left | Control intact | PhS AKG |

[a]PhS, physiological saline
[b]Right and left wing

Experimental Performance

During general anesthetic surgery, the ulnar is broken and optionally denervated. On the first day efter operation saline, AKG or Ala-Gln is administered orally at a dose of 0.8 g/kg body weight in 2 ml.

After the experimental period, the turkeys will be weighed and sacrified in order to measure bone mineral density (BMD).

Bone mineral density (BMD) was analysed by DEXA (Dual Energy X-ray Absorptiometry) using LUNAR apparatus. The method is performed according to Hansen et al. in "Dual-energy x-ray absorptiometry: a precise method of measuring bone mineral density in the lumbal spine (J. Nuci. Med. (1990) 31: 1156-1162), incorporated herein by reference.

Results

In FIG. 13, BMD of the ulna bone is shown for the experimental right wing of the turkeys from group A, and the left wing control. The AKG treatment in the left wing control group gives a 25% difference (p<0.01) compared to the saline treated turkeys in BMD. In the right wing experimental group, the AKG effect is about 11% (p<0.055) compared to the saline treated turkeys.

In FIG. 14, BMD—Vi (Volumetric index) is shown in the ulna bone for the experimental right wing of the turkeys from group A, and the left wing control. The AKG treatment in control group (left wing) gives a 14.8% difference (p<0.01) compared to the saline treated turkeys in BMD. In the experimental (right wing) of the group, the AKG effect is about 35.7% (p<0.01) compared to the saline treated turkeys.

Conclusions

The results show the influence of AKG on the process of ulna bone mineralisation when administrated to the turkey. Also, the effect of AKG is remaining after denerviation of the ulna bone.

Example 3

The Effect of AKG on the Bone Mineralization in Osteopenic Female Rats

Objective

The objective of this example is to study the effect of AKG after postmenopausal bone loss in rats. Ovariectomized rats are used as a preclinical animal model for human postmenopausal osteoporosis, as recommended by the US Food and Drug Administration (FDA).

Animals and Their Maintenance 60 female Wistar rats at the age of 2 months and with an initial bodyweight of 200 g are used.

The animals are maintained in controlled conditions of 12/12 h dark/light ratio at 22° C.±2 and at 55%±2 humidity with free access to food and water.

Experimental Design

The rats are divided into three groups (n=20), where Group 1 is shame operated, Group 2 is ovariectomized and Group 3 is intact, i.e. not operated at all.

Experimental Performance

On the day of surgery, all rats are anaesthetised with an intramuscular injection of ketamine and xylaline.

20 of the rats are shame-operated (SHO), where the ovaries are exteriorised and replaced intact.

The second group of ovariectomized rats (OVX) are submitted to ovariectomy from a dorsal approach.

Six months after ovariectomy, the animals from group 1 and 2, are divided into two additional sub-groups; one placebo and one experimental group.

The content of placebo and experimental drinking water is shown in table 12.

TABLE 12

Content of placebo and experimental drinking water

| Drink components[c] | Placebo drink[a] | Experiment drink[b] |
|---|---|---|
| AKG | — | 146 g |
| Glucose | 300 g | 300 g |
| Sucrose | 150 g | 150 g |
| NaOH | 36 g | 36 g |
| KOH | 7.5 g | 7.5 g |
| Ca(OH)$_2$ | 4.6 g | 4.6 g |
| Mg(OH)$_2$ | 1.8 g | 1.8 g |
| HCl | 75 ml | — |

[a]without AKG
[b]with AKG
[c]all components are dissolved in 10 l of distilled water, pH 4.6

After 60 days with placebo and experimental drinking water the rats are anaesthetised in $CO_2$ and femur isolated for further analysis of bone mineral density.

Results

FIG. 15 shows the bone mineral density in intact (INT), SHO operated and OVX operated rats fed with or without AKG using the drinking water described in Table 12. In all three experimental groups (INT, SHO, OVX), the AKG treated animals shows a higher BMD after AKG treatment with a difference of about 10% between the AKG treated rats and the placebo treated rats (p<0.01 in all groups).

Conclusions

AKG has an effect on ovariectomized rats and increases the BMD to a similar extent as in intact or shame-operated mice.

Example 4

The Effect of AKG on Growth and Bone Mineralisation

Objective

The objective of this example is to study the effect of AKG on growth and bone mineralization of the skeletal system during the postnatal life of the pig.

Animals and Their Maintenance

As in Example 1.

Experimental Design

As in Example 1.

Experimental Performance

Bone mineral density (BMD) was analysed by DEXA (Dual Energy X-ray Absorptiometry) using LUNAR apparatus. The method is performed according to Hansen et al. in "Dual-energy x-ray absorptiometry: a precise method of measuring bone mineral density in the lumbal spine (J. Nucl. Med. (1990) 31: 1156-1162), incorporated herein by reference.

17-beta-estradiol and calcitonin was measured using RIA (Radio-Immuno Assay) using commercially available kits from Orion (Finland), and Diagnostic Systems Laboratories (Webster, Tex., USA) respectively.

Results

FIG. 16 shows the effect of oral administration of AKG on the gain of bodyweight between the AKG treated and Ala-Gln treated groups during the first 47 days of postnatal life. The controle group is not shown, but is always less than the Ala-Gln treated groups at the different timepoints measured. On day three, the difference is about 96 g, on day 14 about 690 g, on day 21 about 419 g, and on day 35 about 313 g. The absolute values of the bodyweight in g is shown below the bars.

Conclusions

Figure 1:
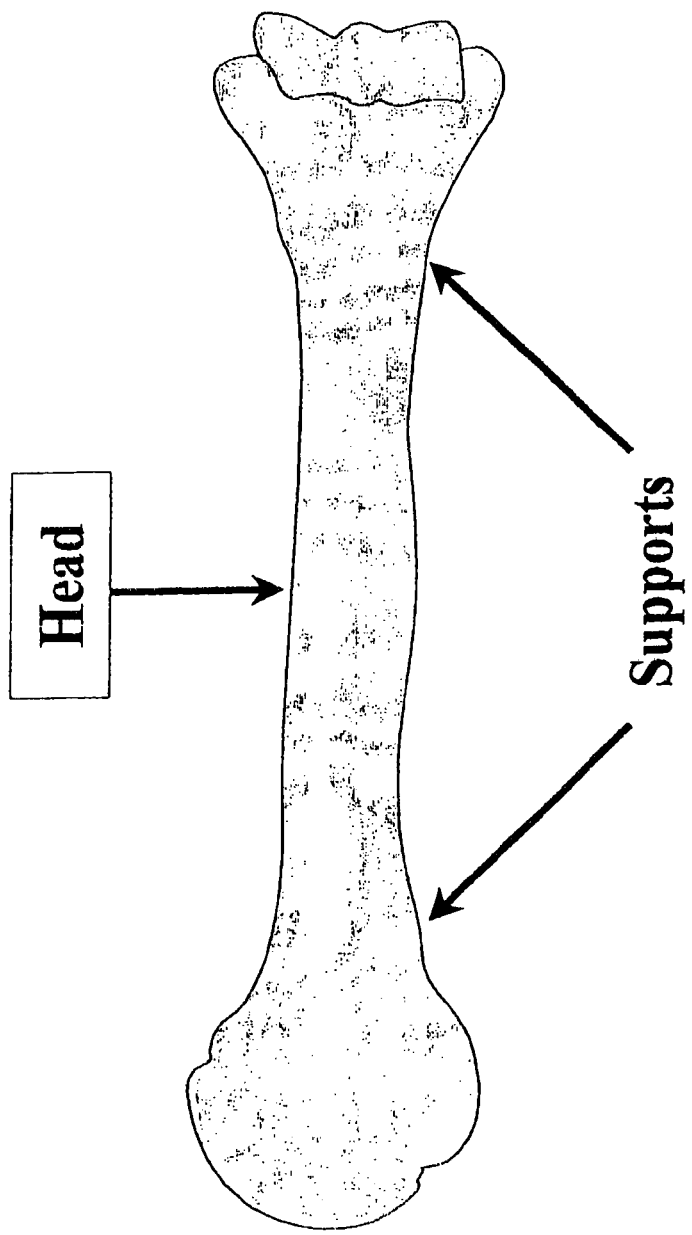
Figure 2:
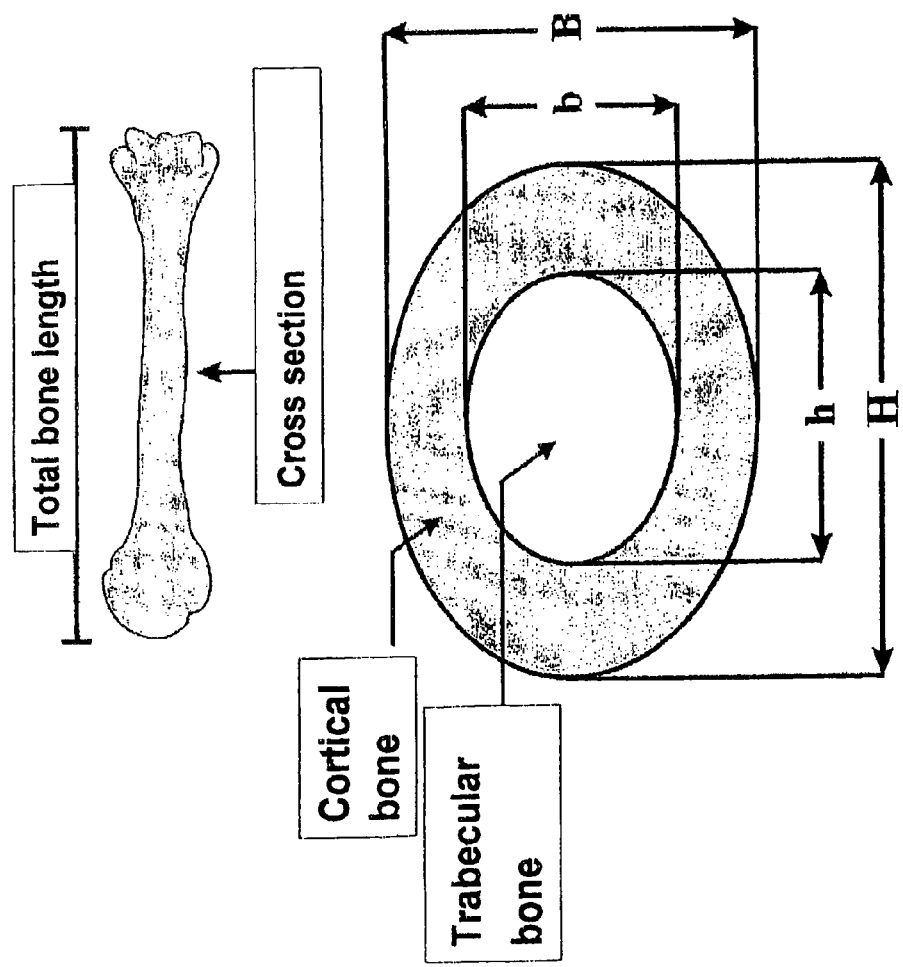
Figure 3:
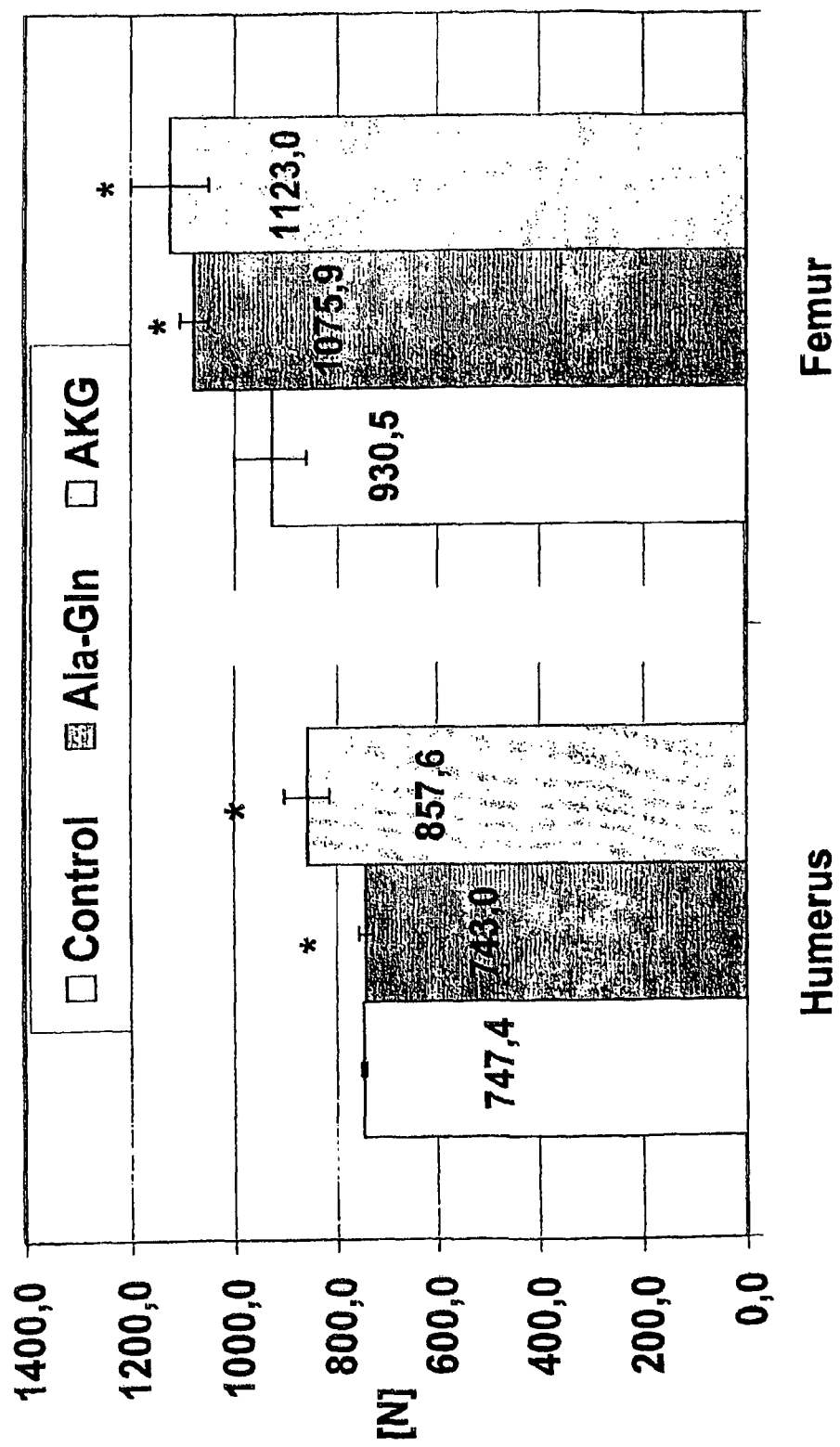
Figure 4:
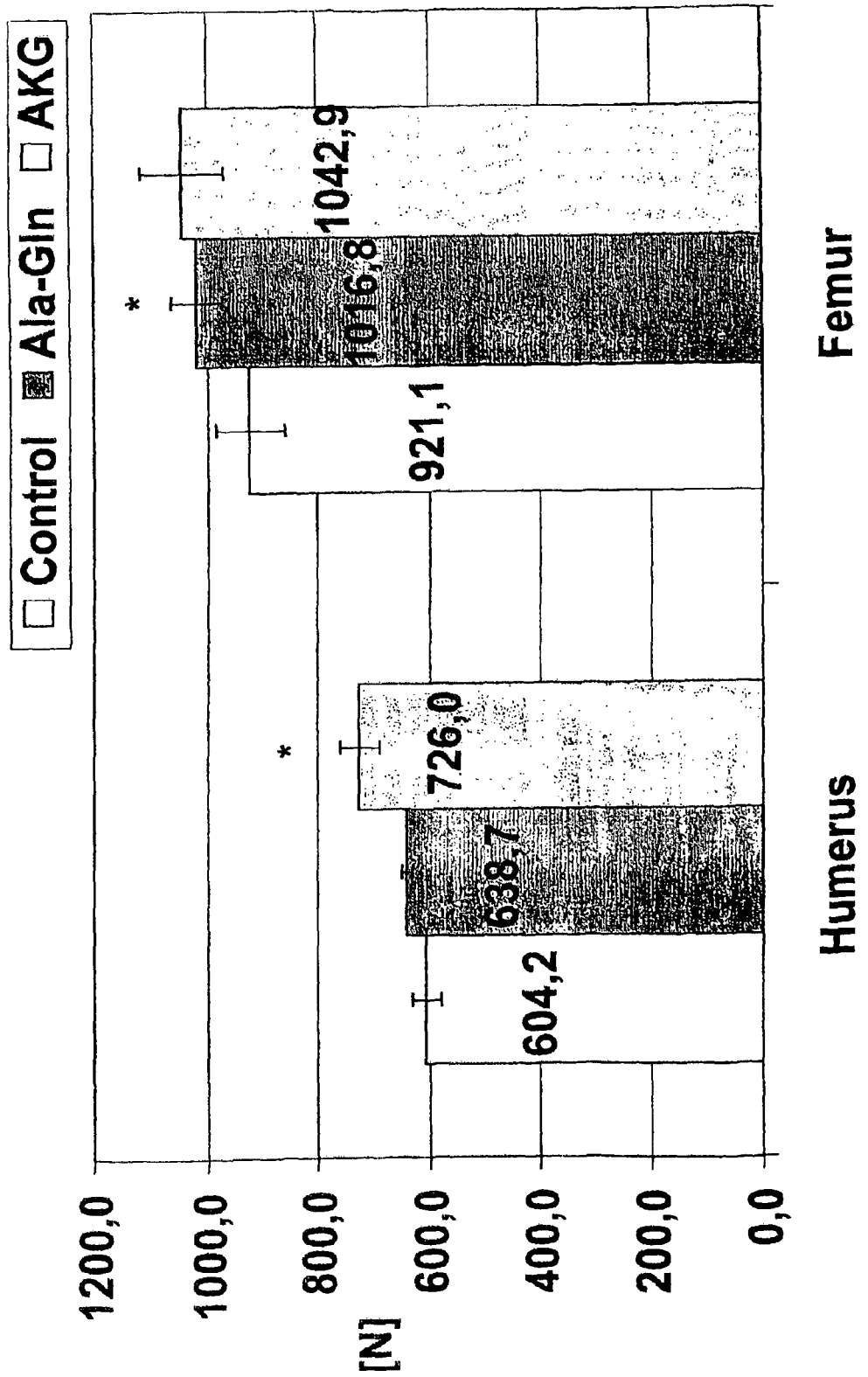
Figure 5:
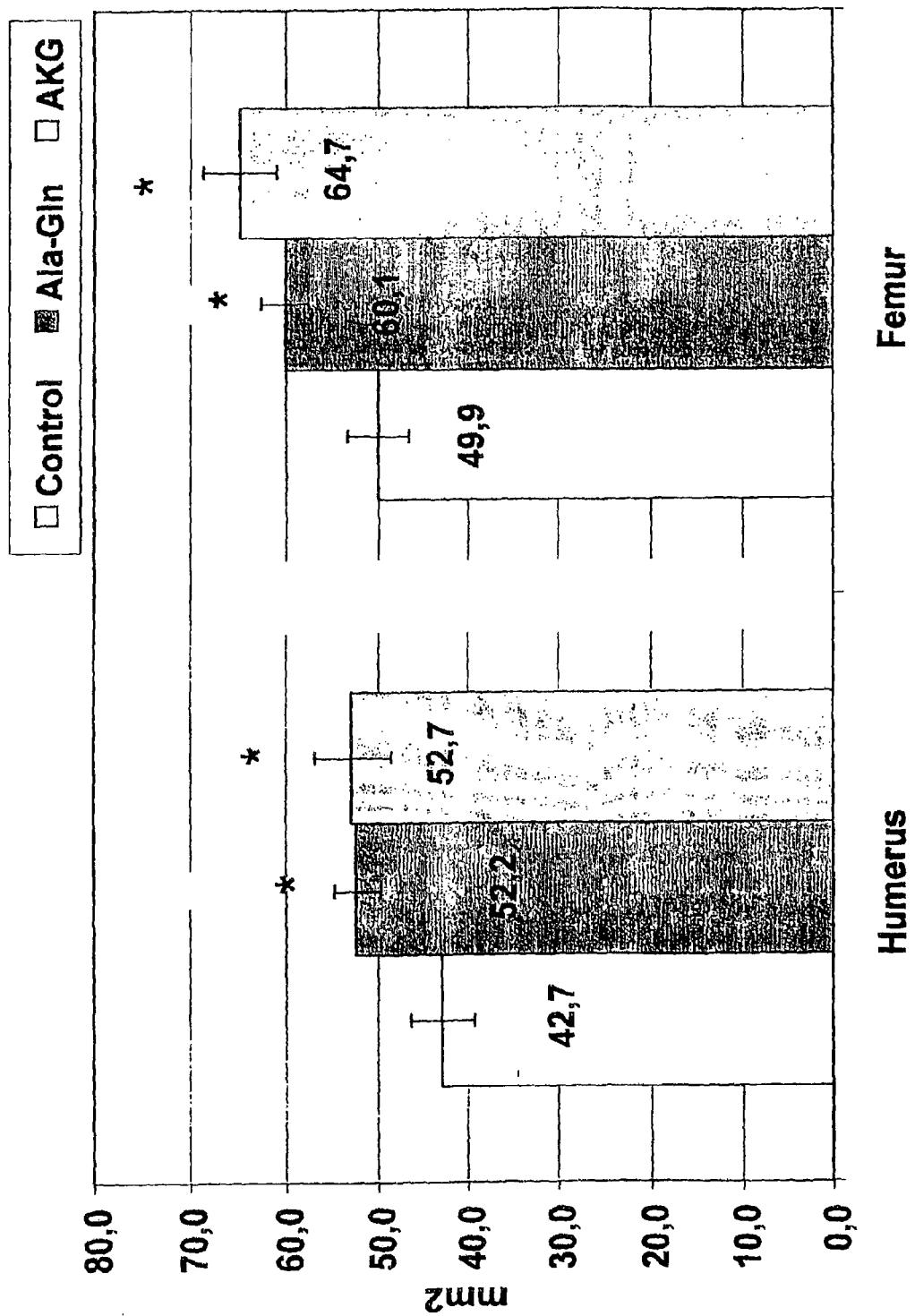
Figure 6:
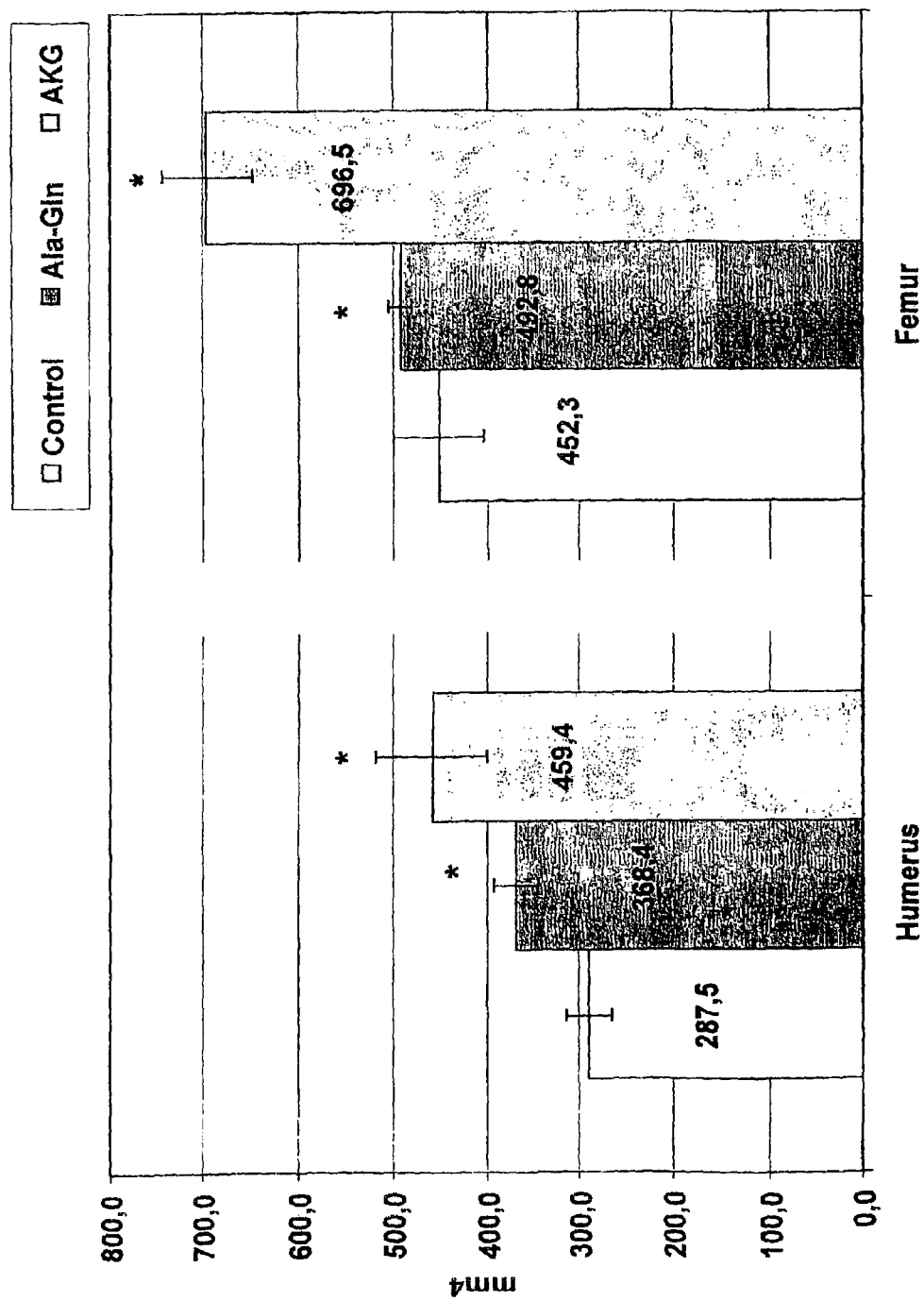
Figure 7:
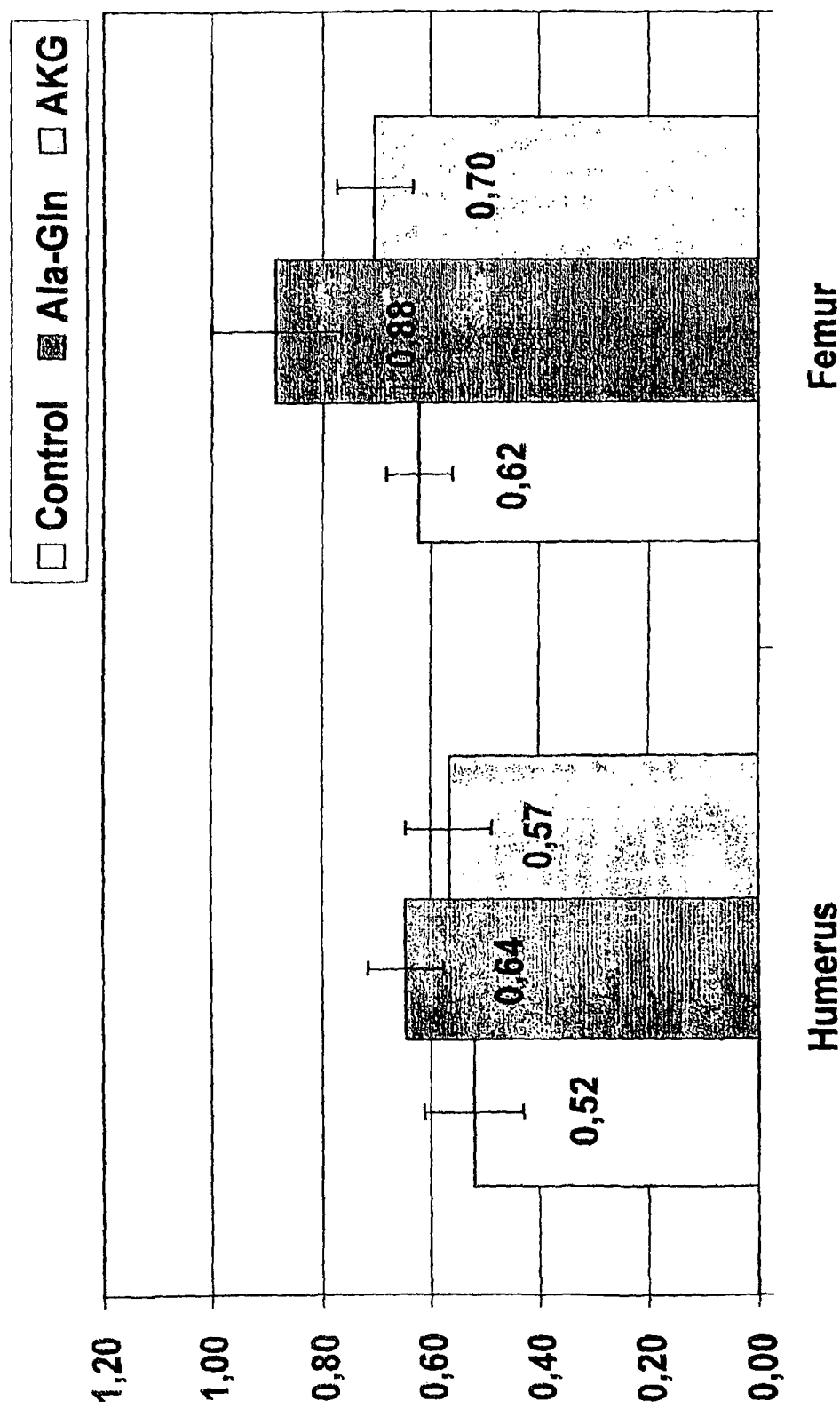
Figure 8:
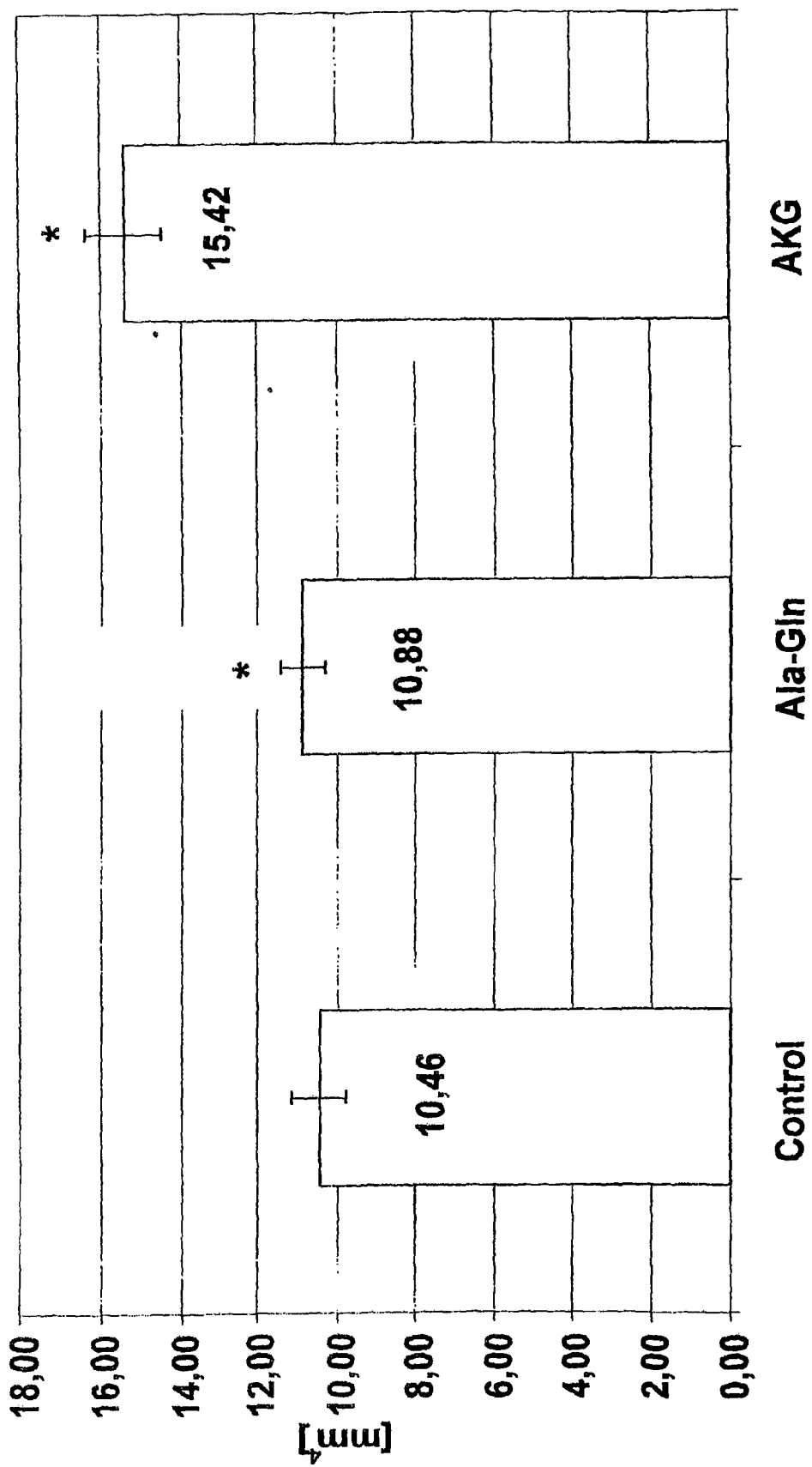
Figure 9:
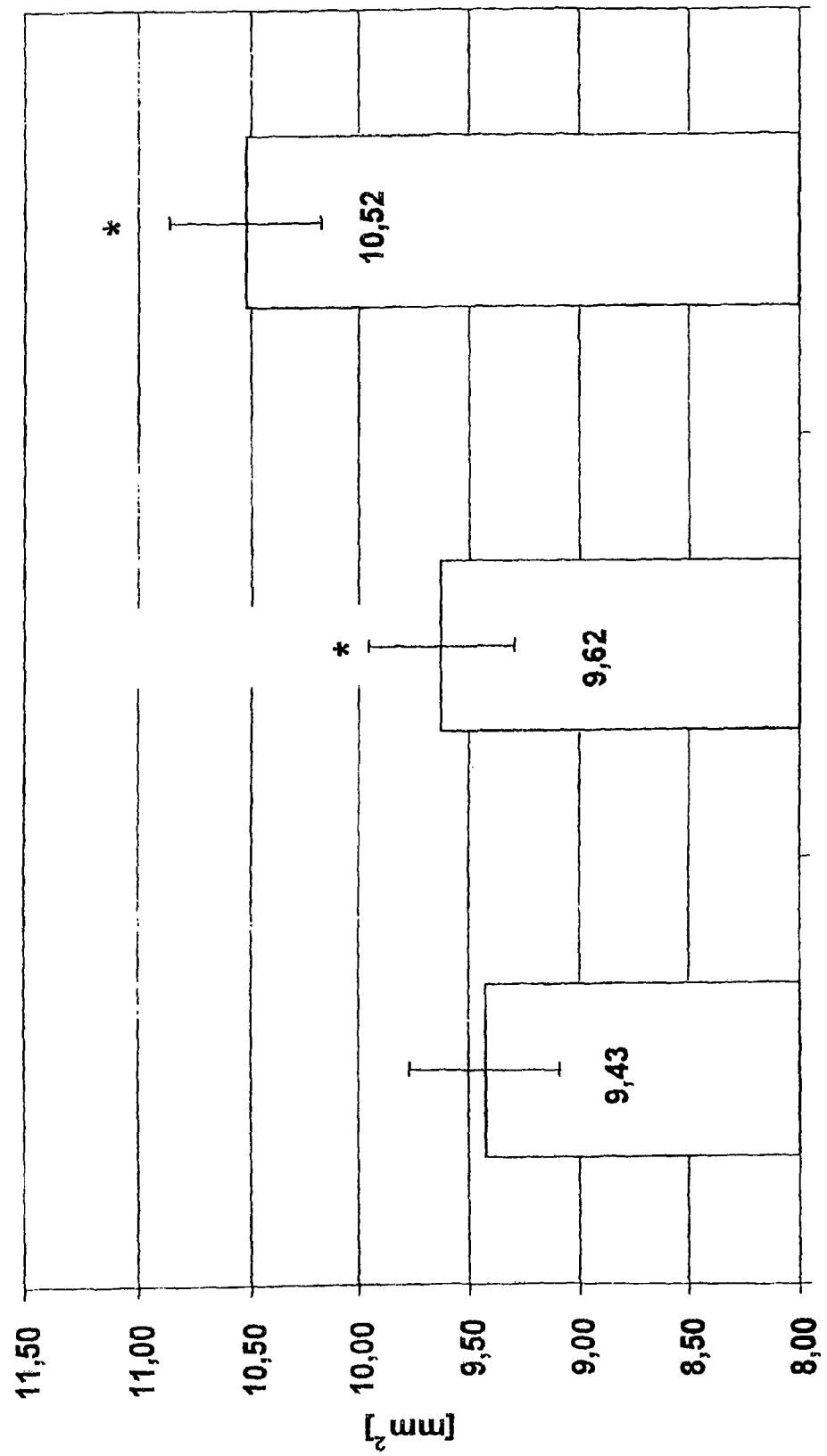
Figure 10:
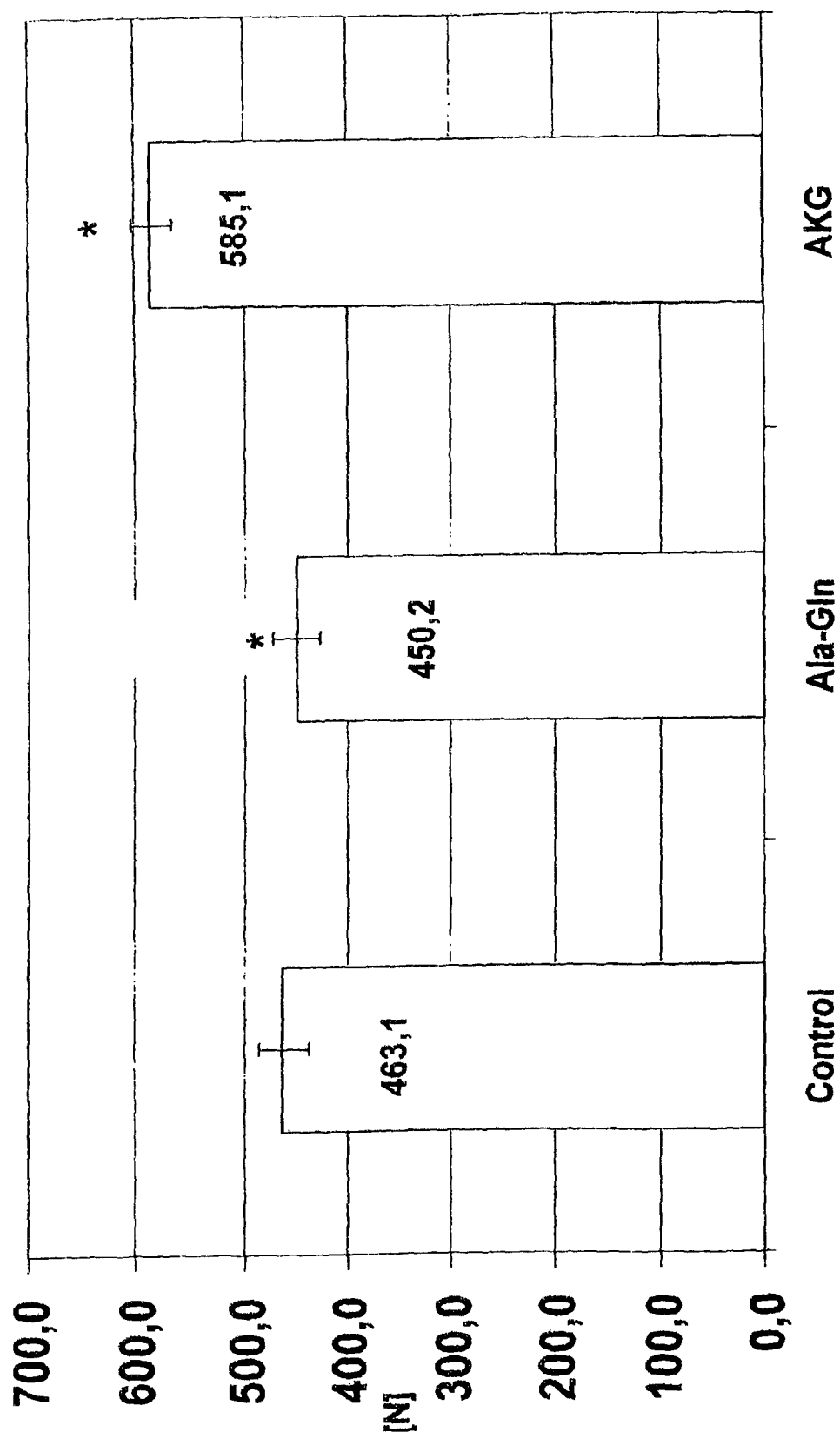
Figure 11:
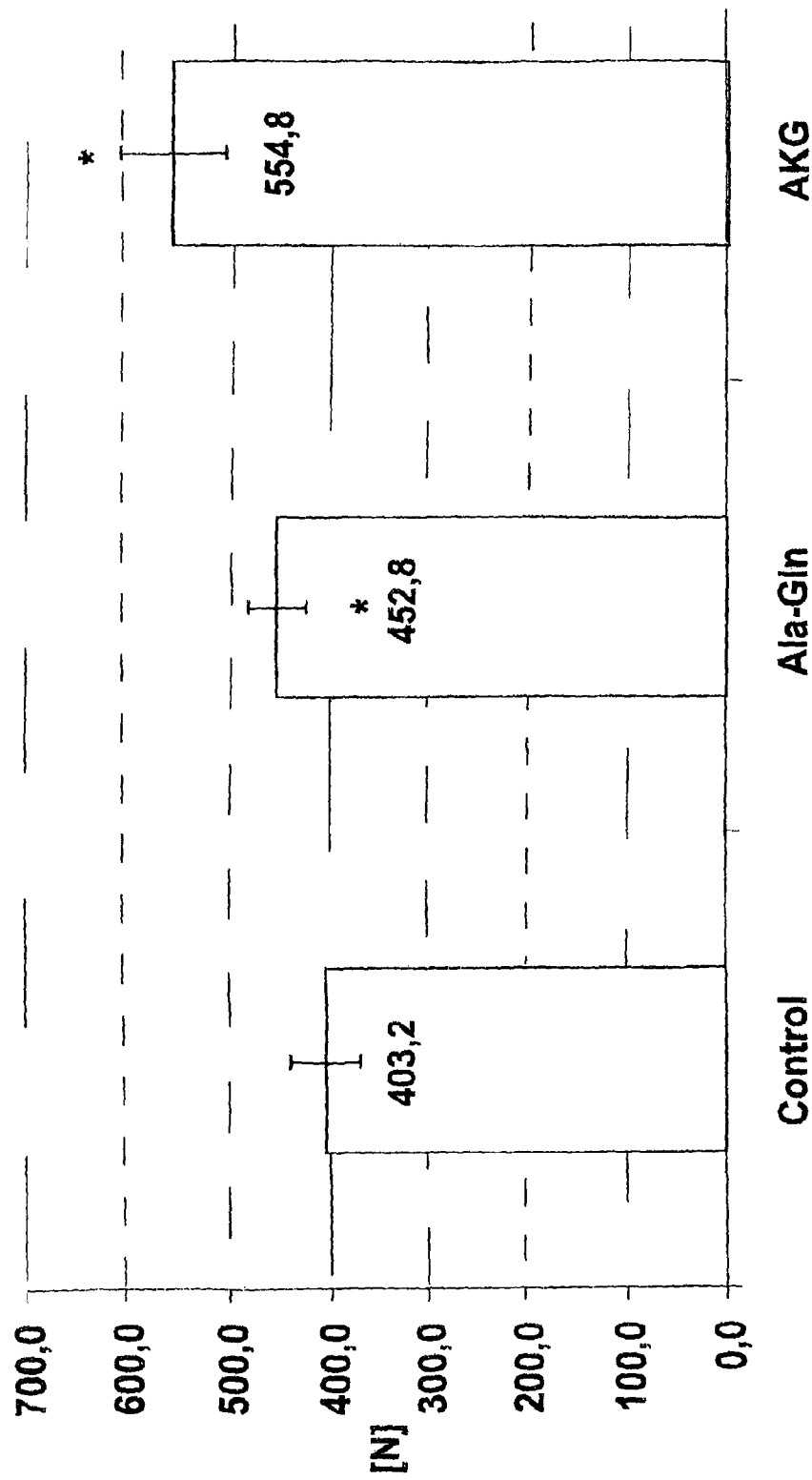
Figure 12:
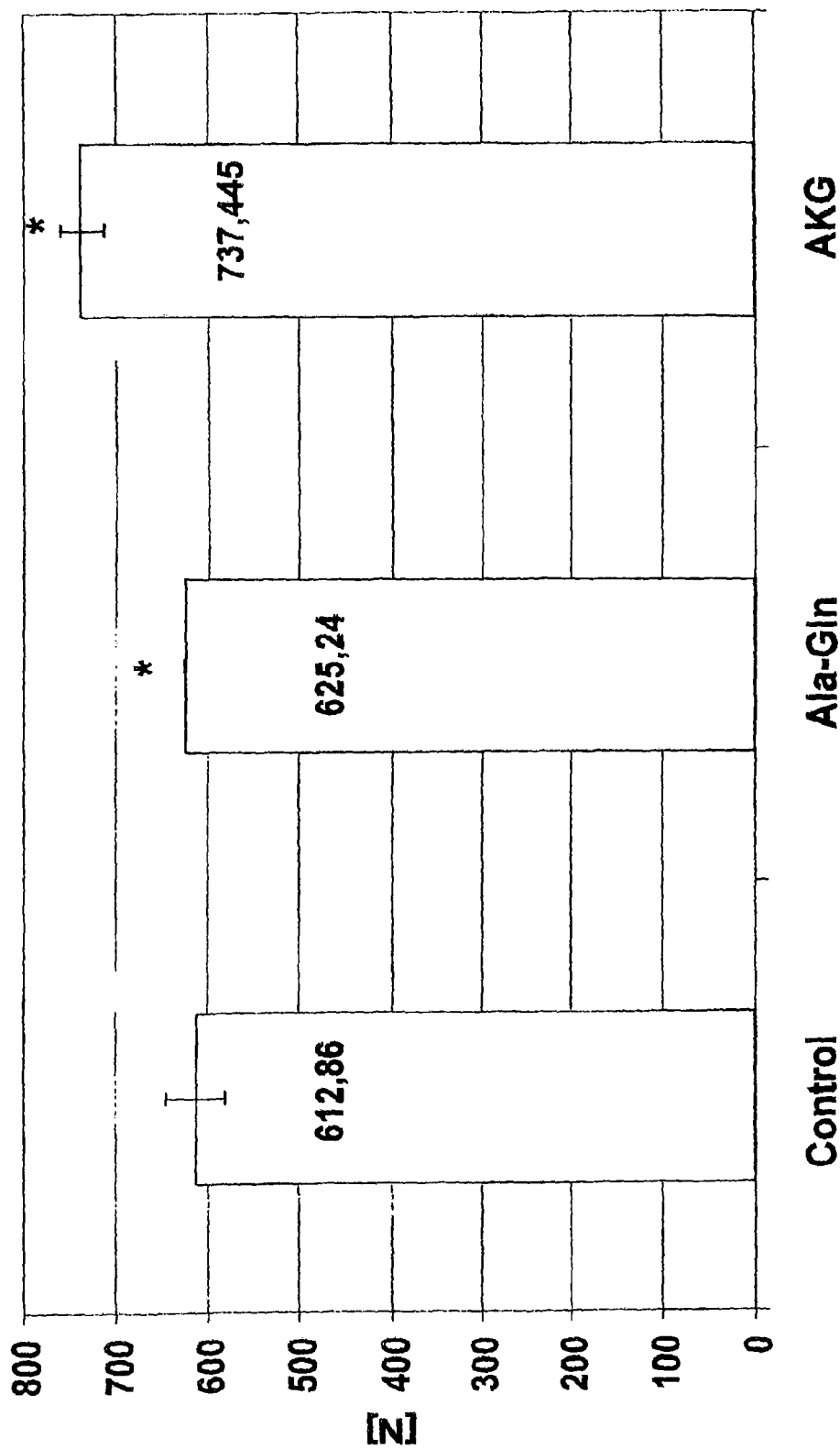
Figure 13:
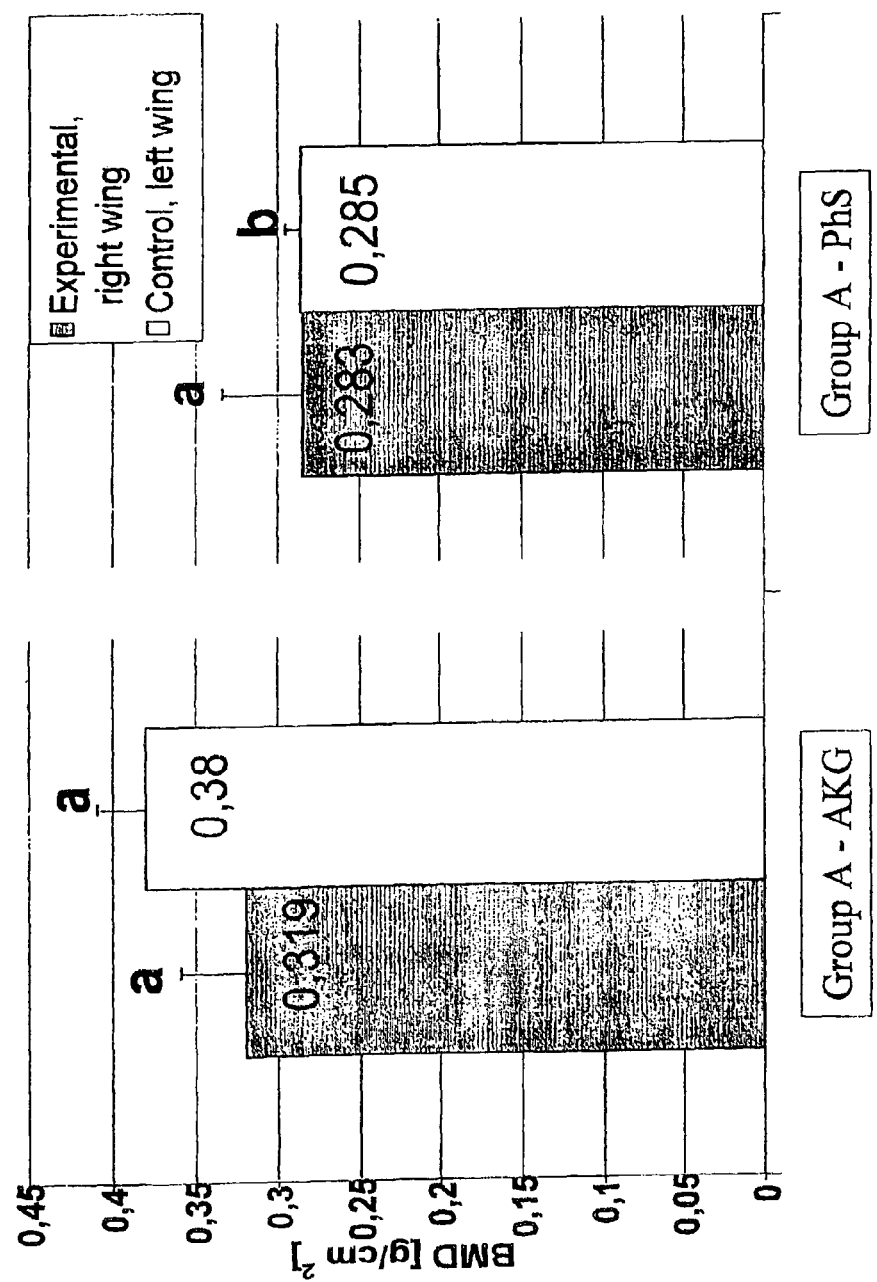
Figure 14:
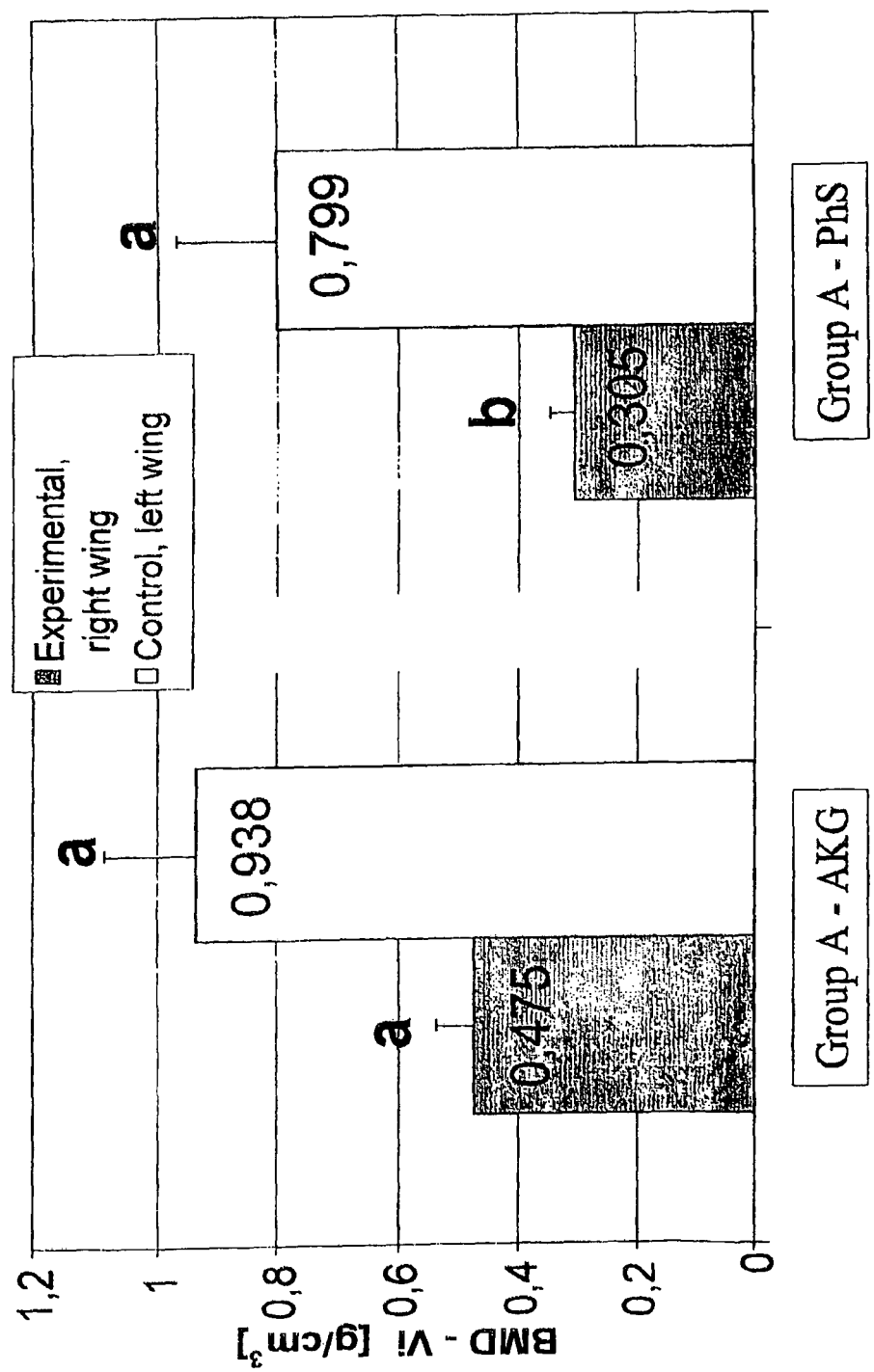
Figure 15:
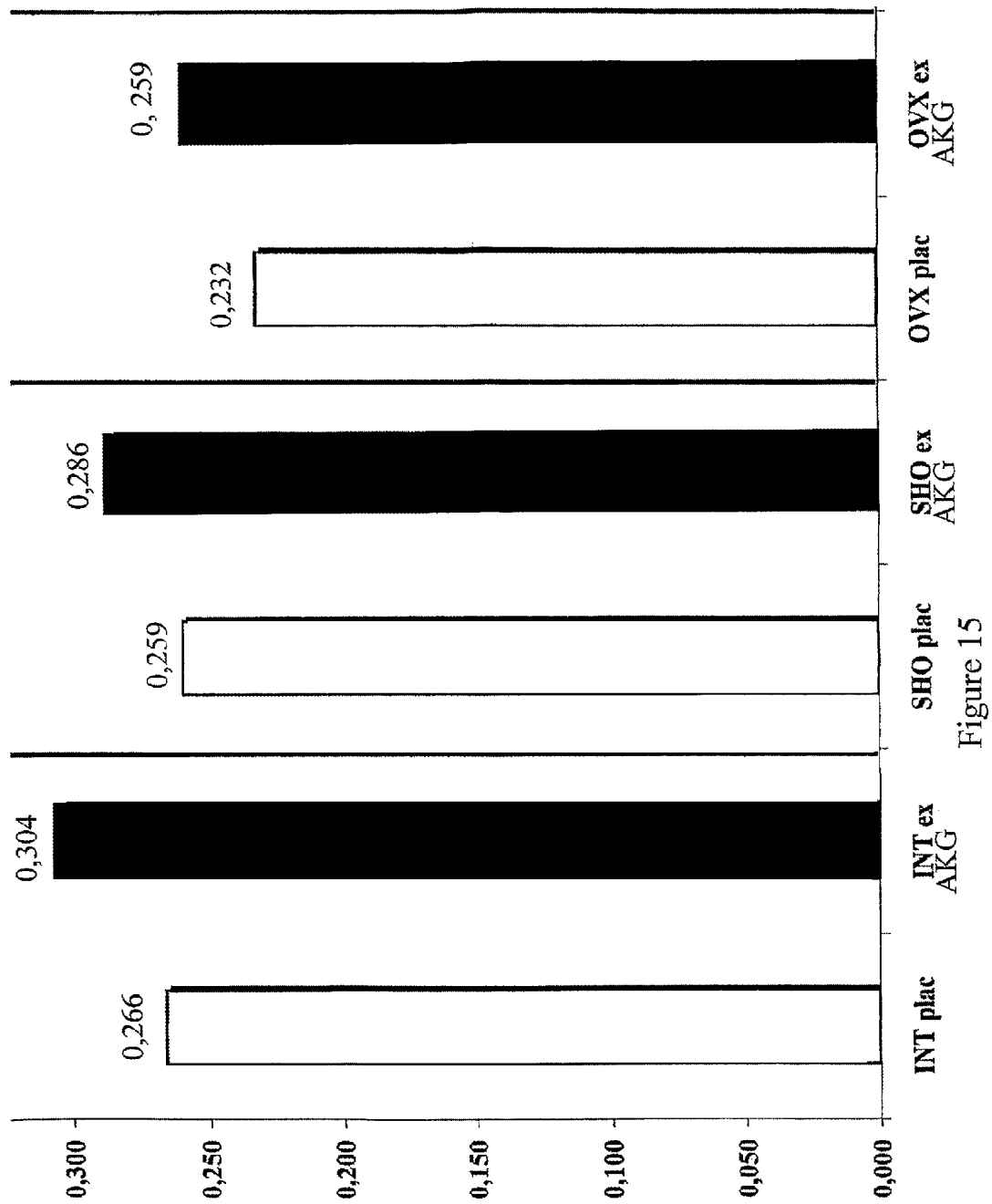
Figure 16:
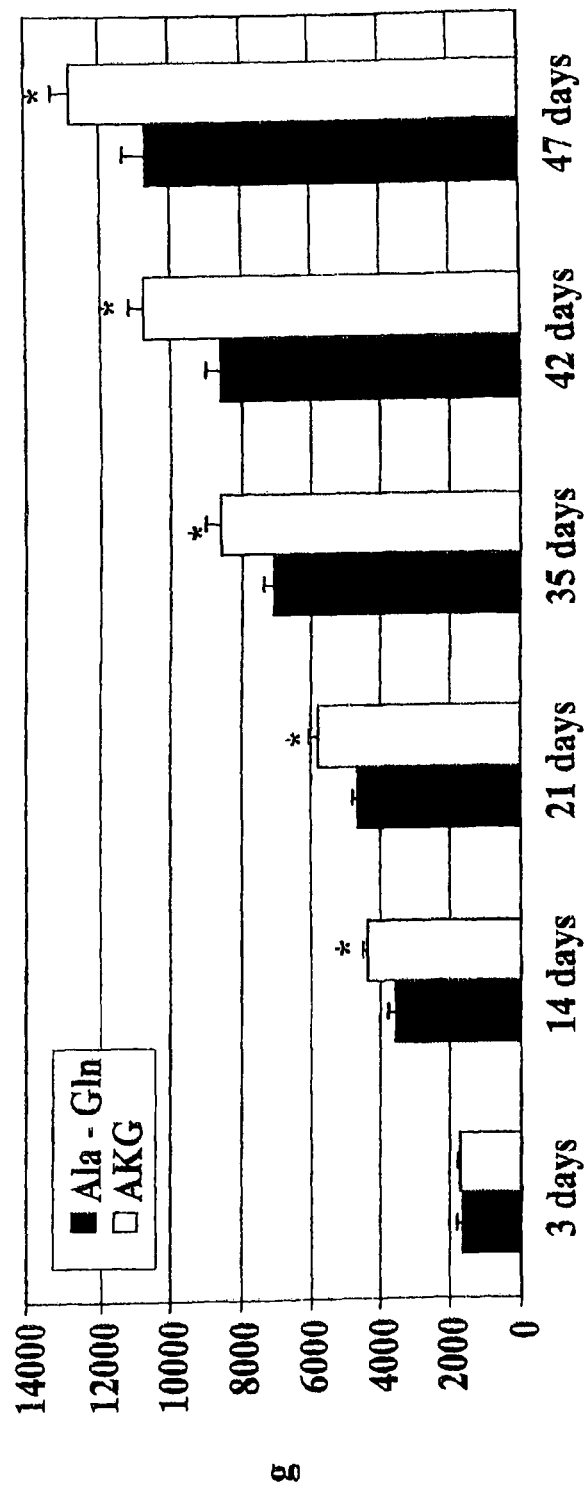
Figure 17:
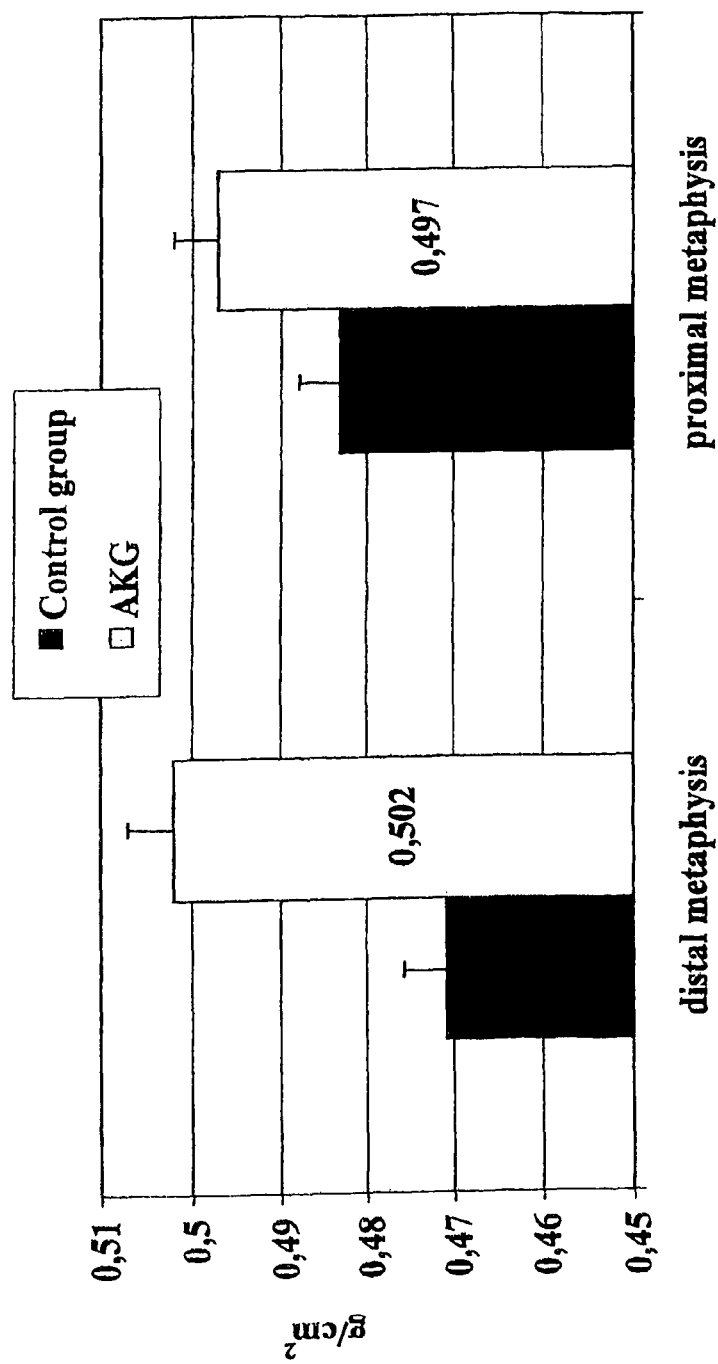
FIG. 17 shows the bone mineral density (BMD) of the right femur at the proximal and distal metaphysis at 21 days of postnatal life.
Figure 18:
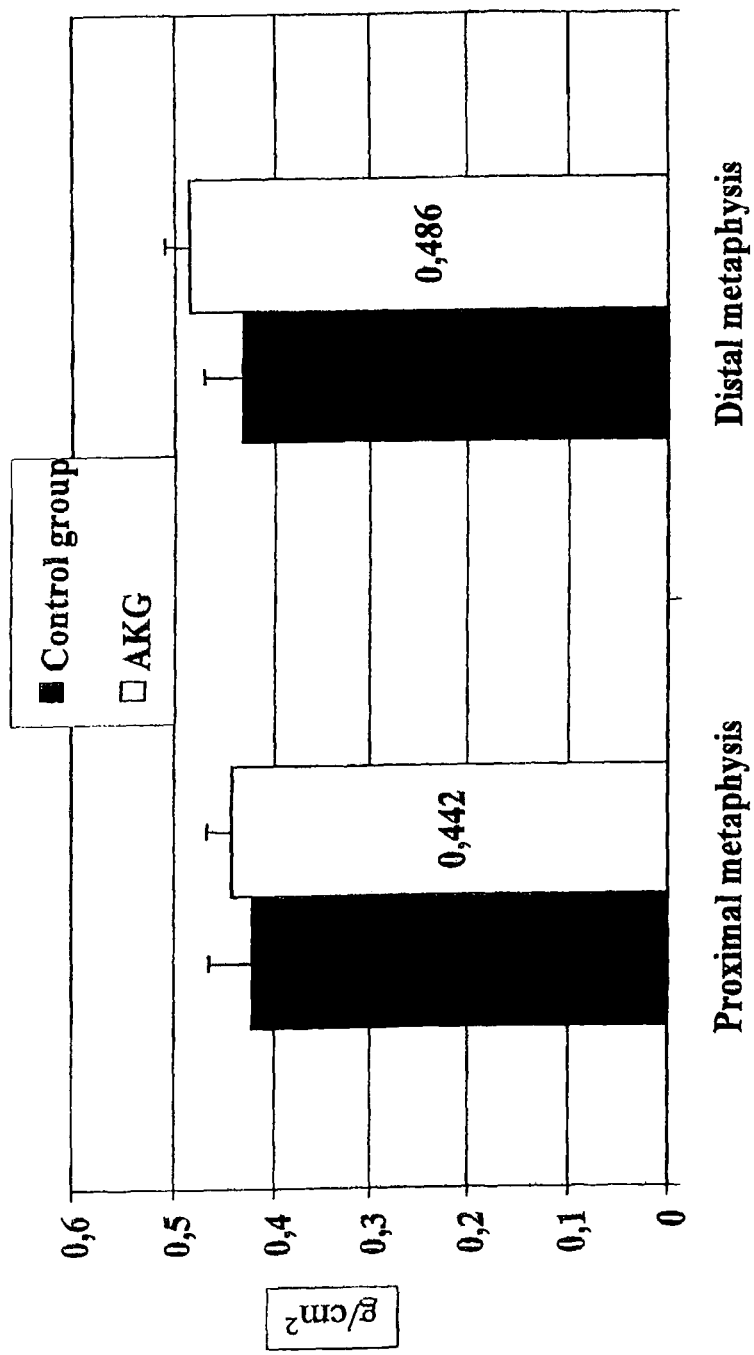
FIG. 18 shows the bone mineral density (BMD) of the right femur at the proximal and distal metaphysis at 35 days of postnatal life.
Figure 19:
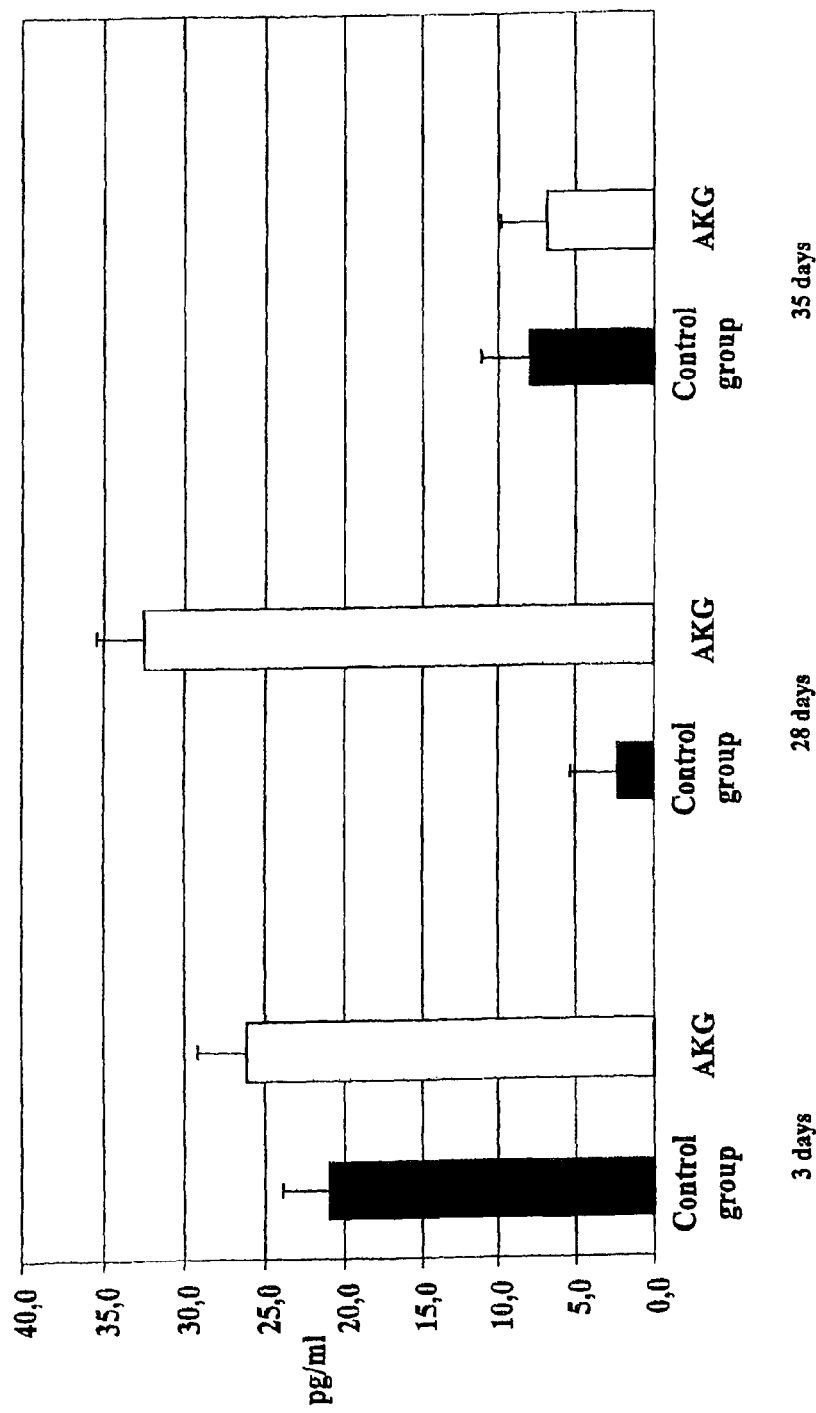
FIG. 19 shows the effect of AKG administration on the level of 17-β-estradiol in blood plasma of piglets measured after 3 days, 28 days, 35 days, 56 days and 70 days. The absolute values of 17-β-estradiol in pg/ml is shown below each bar.
Figure 20:
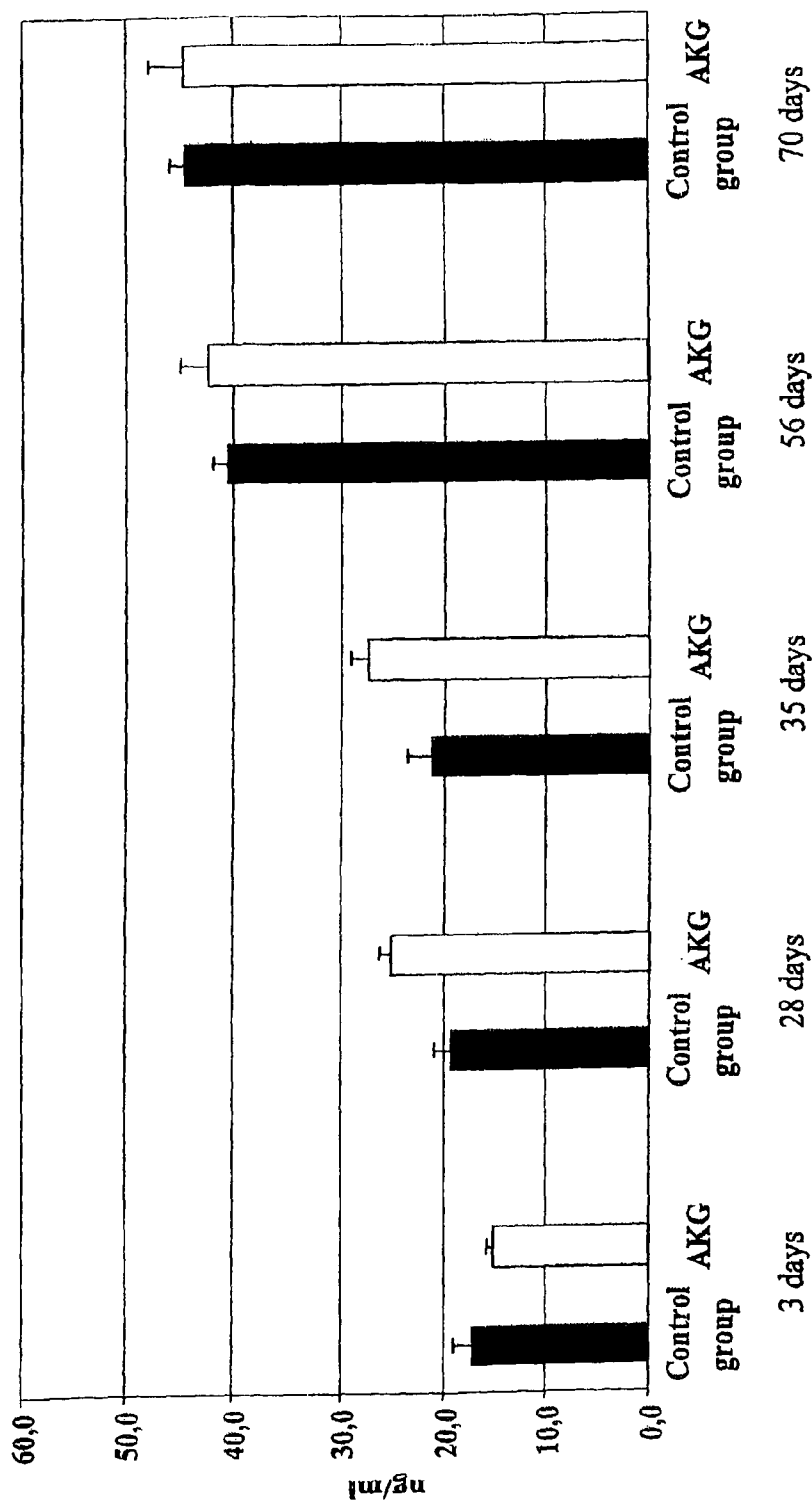
FIG. 20 shows the effect of AKG administration on the level of osteocalcin in blood plasma of piglets measured after 3 days, 28 days, 35 days, 56 days and 70 days. The absolute values of osteocalcin in ng/ml is shown below each bar.
Figure 21:
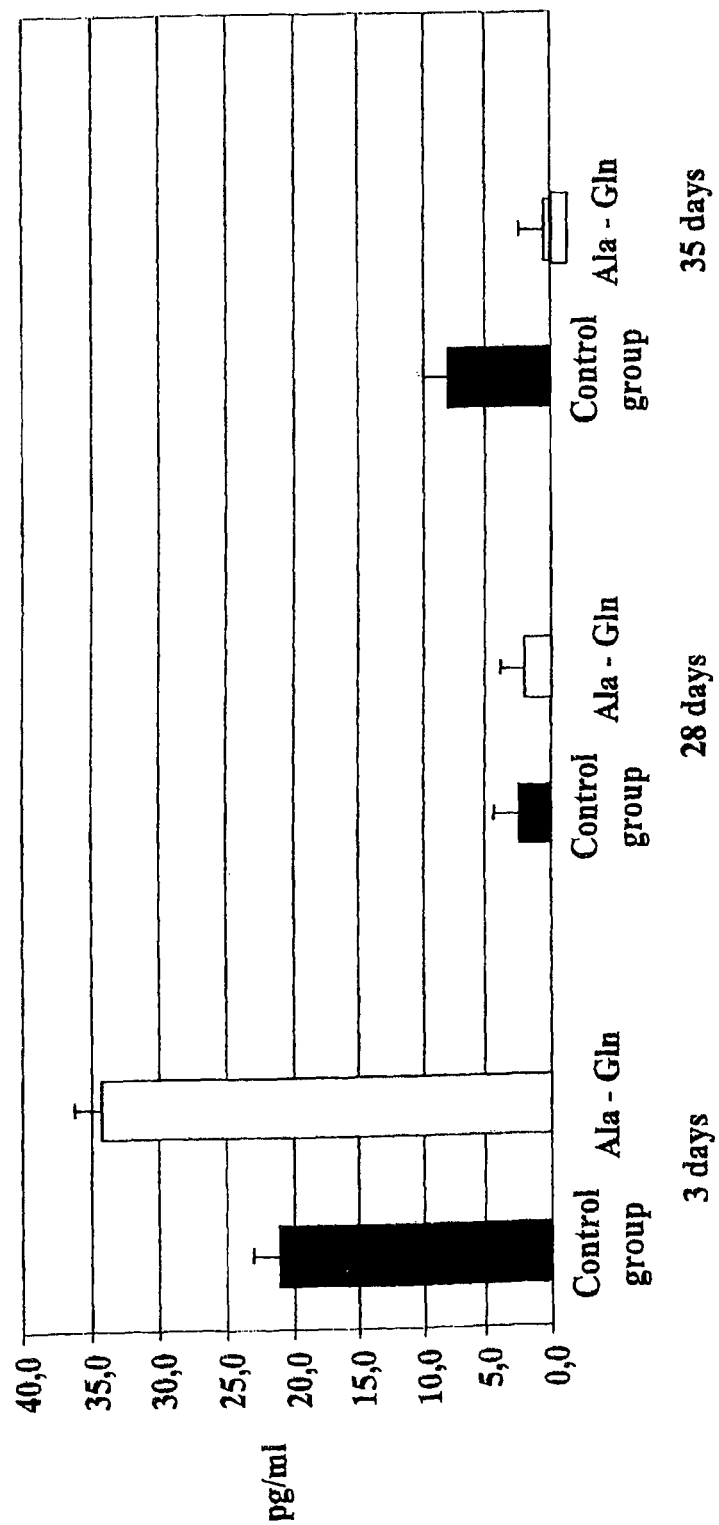
FIG. 21 shows the effect of Ala-Gln administration on the level of 17-β-estradiol in blood plasma of piglets measured after 3 days, 28 days, 35 days, 56 days and 70 days. The absolute values of 17-β-estradiol in pg/ml is shown below each bar.
Figure 22:
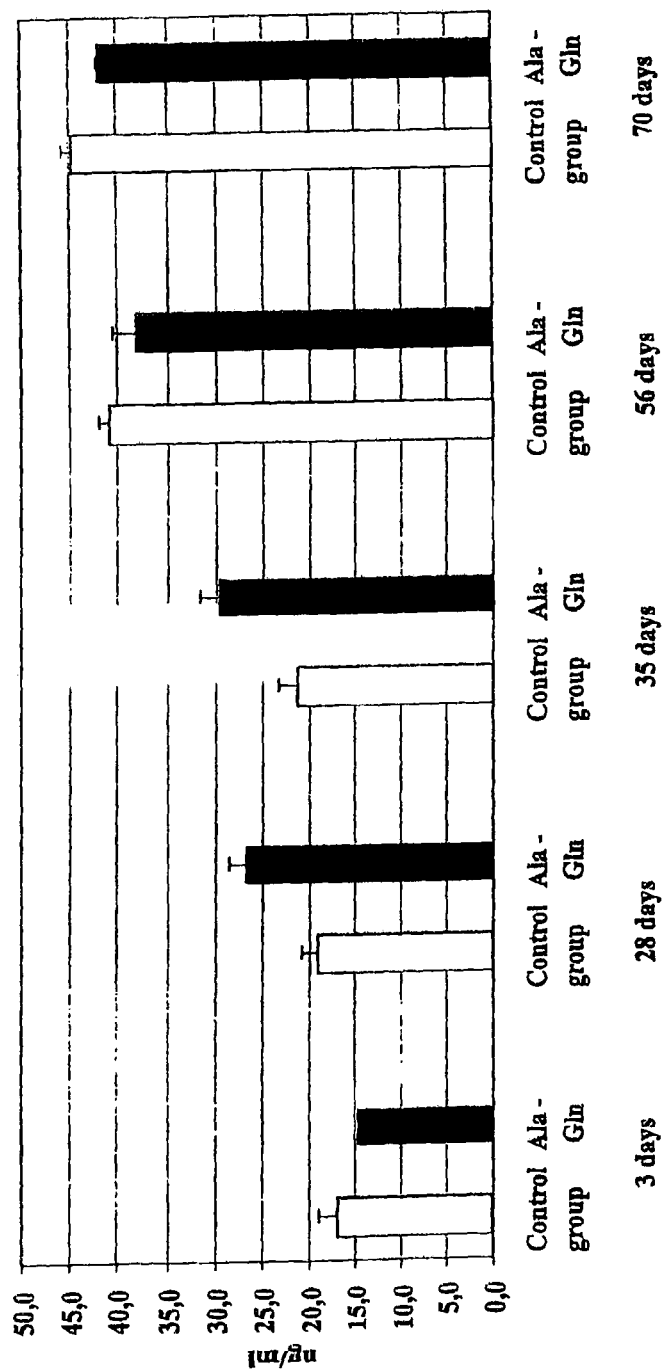
FIG. 22 shows the effect of Ala-Gln administration on the level of osteocalcin in blood plasma of piglets measured after 3 days, 28 days, 35 days, 56 days and 70 days. The absolute values of osteocalcin in ng/ml is shown below each bar.

The bodyweight of the piglets receiving AKG was more dramatic (p>0.01 in comparison to Ala-Gln), than the control group as well as the group receiving Ala-Gln.

Further, the bone mineralisation in piglets receiving AKG was higher than in piglets receiving placebo.

17-β-estradiol and osteocalcin is a measure of maturation and bone formation.

Example 5

The Effect of AKG on Bone Mineralisation in Humans

Objective

The objective of this example is to study the effect of AKG on bone mineralization of the skeletal system in postmenopausal women with decreased bone mineral density (osteopenia).

Study Group of Postmenopausal Women 64 postmenopausal women aged 45-60 years with decreased bone mineral density (osteopenia).

Experimental Design

The study group is randomised in a double blind, parallel group. The patients are randomised to two groups where A) is given AKG+Ca and B) is given placebo+Ca as shown in table 13.

Tablets are given for 24 weeks and the dose stable during the study time, i.e. 6 g of AKG+1.68 g Ca daily or placebo+1.68 g Ca daily.

All patients will take chewable tablets three times daily; during breakfast, lunch and dinner, where each tablet comprises 1 g AKG+0.28 g Ca or placebo+0.28 g Ca. The tablets should be chewed and be taken just before intake of the meal.

TABLE 13

| Study group | Daily drug dosage (amount) |
| --- | --- |
| A | AKG (6 g) + Ca (1.68 g)[a] |
| B | Placebo + Ca (1.68 g)[a] |

[a]Vehiculum: Corn starch and microcrystalline cellulose

Results

Serum levels of osteocalcin and CTX is used as bone turnover markers and measured by Enzyme Linked Immunosorbent Assay (ELISA). Bone mineral density is measured by Dual Energy X-ray Absorptionmetry (DEXA, DPX, LUNAR Corp., USA) technique in lumbar spine.

The above outlined experimental design has in our hands proven successful in humans.

The invention claimed is:

1. A method of reducing the risk of or treating osteoporosis, the method comprising:
   administering a composition comprising alpha-ketoglutaric acid (AKG) or a pharmaceutically acceptable salt thereof, to a vertebrate in need thereof, wherein the composition is administered at 0.01-0.2 g/kg bodyweight per daily dose.

2. The method according to claim 1, wherein the composition further comprises a pharmaceutically acceptable carrier and/or additives.

3. The method according to claim 1, wherein the composition is a food or a feed supplement.

4. The method according to claim 1 wherein the composition is a dietary supplement and/or a component in the form of solid food and/or beverage.

5. A method of improving bone quality in a vertebrate, comprising:
   administering a composition comprising alpha-ketoglutaric acid (AKG) or a pharmaceutically acceptable salt thereof, to a vertebrate in the need thereof, wherein the composition is administered at 0.01-0.2 g/kg bodyweight per daily dose.

6. The method according to claim 5, wherein the composition further comprises pharmaceutically acceptable carrier and/or additives.

7. The method according to claim 5, wherein the composition is a food or a feed supplement.

8. The method according to claim 5, wherein the composition is a dietary supplement and/or a component in form of solid food and/or beverage.

9. The method according to claim 1, wherein the pharmaceutically acceptable salt thereof is a mono- or di-metal salt of alpha-ketoglutaric acid (AKG).

10. The method according to claim 1, wherein the pharmaceutically acceptable salt thereof is an amino-acid salt of alpha-ketoglutaric acid (AKG).

11. The method according to claim 5, wherein the pharmaceutically acceptable salt thereof is a mono- or di-metal salt of alpha-ketoglutaric acid (AKG).

12. The method according to claim 5, wherein a pharmaceutically acceptable salt thereof is an amino-acid salt of alpha-ketoglutaric acid (AKG).

13. The method according to claim 1, wherein the vertebrate is affected with osteoporosis.

14. The method according to claim 5, wherein the vertebrate is affected with osteoporosis.

15. A method of treating osteopenia and preventing osteoporosis, the method comprising:
   administering a composition comprising alpha-ketoglutaric acid (AKG) or a pharmaceutically acceptable salt thereof, to a vertebrate in need thereof, wherein the composition is administered at 0.01-0.26 g/kg bodyweight per a daily dose.

16. The method according to claim 15, wherein the composition further comprises a pharmaceutically acceptable carrier and/or additives.

17. The method according to claim 15, wherein the composition is a food or a feed supplement.

18. The method according to claim 15, wherein the composition is a dietary supplement and/or a component in the form of solid food and/or beverage.

19. The method according to claim 15, wherein the pharmaceutically acceptable salt thereof is a mono- or di-metal salt of alpha-ketoglutaric acid (AKG).

20. The method according to claim 15, wherein the pharmaceutically acceptable salt thereof is an amino-acid salt of alpha-ketoglutaric acid (AKG).

21. The method according to claim 5, wherein the vertebrate is a mammal or a bird.

22. The method according to claim 1, 5, or 15, wherein the a composition comprising AKG or a pharmaceutically acceptable salt thereof further comprises glutamine.

23. The method according to claim 1, 5, or 15, wherein the a composition comprising AKG or a pharmaceutically acceptable salt thereof further comprises ornithine.

* * * * *